US007276646B1

(12) United States Patent
Fogher

(10) Patent No.: US 7,276,646 B1
(45) Date of Patent: Oct. 2, 2007

(54) SYNTHETIC POLYNUCLEOTIDE CODING FOR HUMAN LACTOFERRIN, VECTORS, CELL AND TRANSGENIC PLANTS CONTAINING IT

(75) Inventor: Corrado Fogher, Casalmaggiore (IT)

(73) Assignee: Plantechno S.r.l., Casalmaggiore CR (IT)

(*) Notice: Subject to any disclaimer, the term of this patent is extended or adjusted under 35 U.S.C. 154(b) by 0 days.

(21) Appl. No.: 09/743,823

(22) PCT Filed: Jul. 19, 1999

(86) PCT No.: PCT/IT99/00226

§ 371 (c)(1),
(2), (4) Date: Aug. 22, 2001

(87) PCT Pub. No.: WO00/04146

PCT Pub. Date: Jan. 27, 2000

(30) Foreign Application Priority Data

Jul. 17, 1998 (IT) .............................. RM98A0478

(51) Int. Cl.
C12N 15/82 (2006.01)
A01H 5/00 (2006.01)
A23C 11/10 (2006.01)
A23L 1/00 (2006.01)

(52) U.S. Cl. ...................... 800/288; 800/293; 800/294; 800/298; 800/312; 800/317; 800/317.3; 800/32 C; 800/320.2; 435/320.1; 435/419; 435/430.1; 435/469; 435/470; 435/69.1; 426/46; 426/598; 426/622; 426/629; 426/634

(58) Field of Classification Search ............. 435/320.1, 435/419, 468, 469, 470; 800/287, 288, 298, 800/293, 294
See application file for complete search history.

(56) References Cited

U.S. PATENT DOCUMENTS 6,569,831 B1 * 5/2003 Legrand et al. ............... 514/12

FOREIGN PATENT DOCUMENTS

WO 91/13993 9/1991
WO 96/37094 11/1996
WO 98/06860 2/1998

OTHER PUBLICATIONS

Mitra A. et al. Expression of a human lactoferrin cDNA in tobacco cells produces antibacterial protein(s). Plant Physiol. Nov. 1994;106(3):977-81.*
Salmon V. et al. Production of Human Lactoferrin in Transgenic Tobacco Plants, Protein Expression and Purification, vol. 13, Issue 1, pp. 127-135, Jun. 1998.*
Shen Q. et al. Modular nature of abscisic acid (ABA) response complexes: composite promoter units that are necessary and sufficient for ABA induction of gene expression in barley. Plant Cell. Jul. 1996;8(7):1107-1119.*
Watanabe Y. et al. Nucleotide sequence of the basic 7S globulin gene from soybean. Plant Physiol. Jul. 1994;105(3):1019-20.*
Parmenter D.L. et al. Production of biologically active hirudin in plant seeds using oleosin partitioning. Plant Mol Biol. Dec. 1995;29(6):1167-80.*
van der Geest A. et al. A 68 bp element of the beta-phaseolin promoter functions as a seed-specific enhancer. Plant Mol Biol. Nov. 1996;32(4)579-88.*
van der Geest A. et al. A 68 bp element of the beta-phaseolin promoter functions as a seed-specific enhancer. Plant Mol Biol. Nov. 1996;32(4):579-88.*
Kagawa H. et al. Sequence of a cDNA encoding soybean basic 7S globulin. Nucleic Acids Res. Nov. 11, 1989;17(21):8868.*
Shu T.F. et al. GenBank Accession U59425, Glycine max 7S seed globulin precursor, mRNA, complete cds. Jul. 3, 1996.*
Mollet B. et al. Functional foods: at the frontier between food and pharma. Curr Opin Biotechnol. Oct. 2002;13(5):483-85.*
Roberfroid M.B. Concepts and strategy of functional food science: the European perspective. Am J Clin Nutr. Jun. 2000;71(6 Suppl):1660S-4S; discussion 1674S-5S. Review.*
Roberfroid M.B. Concepts in functional foods: the case of insulin and oligofructose. J Nutr. Jul. 1999;129(7 Suppl): 1398S-401S. Review.*
Salmon, et al., "Production of Human Lactoferrin in Transgenic Tobacco Plants," XP000863470, *Protein Expression and Purification 13*, Article PT980886, pp. 127-135 (1998).
Mitra, et al., "Expression of a Human Lactoferrin cDNA in Tobacco Cells Produces Antibacterial Protein (s)," XP002048441, *Plant Physiol.*, pp. 977-981 (1994).
Ward, et al., "A System for Production of Commercial Quantities of Human Lactoferrin: A Broad Spectrum Natural Antibiotic," XP002048442, *Biotechnology* vol. 13, pp. 498-503 (1995).
Zhang, et al., Abstact of "Development of Transgenic Plants with Non-Plant Antibacterial Protein Genes for Resistance to Bacterial Pathogens Lactoferrin, Nicotiana Tabacum, Agrobacterium Tumefaciens," XP002048439, *Dissertation Abstracts International* (1996).
Watanabe, et al., "Nucleotide Sequence of the Basic 7S Globulin Gene from Soybean," XP002125177, *Plant Physiol.*, pp. 1019-1020 (1994).
Lonnerdal, B. and S. Iyer, "Lactoferrin: Molecular Structure and Biological Function," *Annu. Rev. Nutr.*, vol. 15, pp. 93-110 (1995).
Okita, T.W. and J.C. Rogers, "Compartmentation of Proteins in the Endomembrane System of Plant Cells," *Annu. Rev. Plant Physiol. Plant Mol. Biol.*, vol. 47, pp. 327-350 (1996).
Pen, J., "Comparison of Host Sytstems for the Production of Recombinant Proteins," *Transgenic Plants: A Production System for Industrial and Pharmaceutical Proteins*, J. Wiley & Sons, New York, Eds. M.R.L. Owen and J. Pen, Ch. 4, pp. 149-167 (1996).
Shewry, P.R., et al., "Seed Storage Proteins: Structures and Biosynthesis," *The Plant Cell*, vol. 7, pp. 945-956 (Jul. 1995).
Stowell, K.M., et al., "Expression of cloned human lactoferrin in baby-hamster kidney cells," *Biochem. J.*, vol. 276, pp. 349-355 (1991).

* cited by examiner

*Primary Examiner*—Cynthia Collins
(74) *Attorney, Agent, or Firm*—Nixon & Vanderhye P.C.

(57) ABSTRACT

A synthetic polynucleotide encoding human lactoferrin, modified with respect to the natural gene so as to maximize its expression in vegetals, on the basis of the preferential use of the codons is described. Moreover, the vectors containing such sequence, that having regulation elements activated in a controlled way determine its tissue- and stage-specific expression are further described. The vegetal cells and the plants transformed with the afore mentioned vectors, as well as the production processes of functional foods, vegetal milks, and human lactoferrin, utilizing them are also described.

42 Claims, 13 Drawing Sheets

FIG. 6

SYNTHETIC POLYNUCLEOTIDE CODING FOR HUMAN LACTOFERRIN, VECTORS, CELL AND TRANSGENIC PLANTS CONTAINING IT

FIELD OF THE INVENTION

The present invention relates to the field of the vegetable biotechnologies, and in particular to the plants and vegetal cells transformation techniques and systems, to cells and transgenic plants thus generated, and to their use.

STATE OF THE ART

In recent years, due to the large variety of applications deriving from the utilization of the genetic engineering techniques in the biology of the vegetals, the use of genetically modified plants has gradually increased.

In particular, the development of techniques for the transformation of plants into organisms capable of producing proteins of commercial interest has acquired a remarkable practical importance.

In fact, the generation of recombinant plants containing a heterologous gene of interest, and their use in production processes on an industrial scale, allows to overcome a series of drawbacks characterizing the production systems presently in use, particularly those based on cell cultures.

Indeed, recombinant DNA technology allowed the generation of transgenic cells that are used in the production of heterologous proteins of interest. In particular, animal (and specifically mammal) cell cultures allow the production of proteins of interest, even extremely complex ones, in their native form, but the related process is extremely expensive, as hectoliters of cells are required for the production of an amount of proteins sufficient for a commercial (e.g., pharmacological or alimentary) use (Stowell et al., 1991).

An alternative in this direction is then provided by the production, carried out in prokaryotic cell cultures, a cheaper process, meeting however a serious obstacle in the inability of those systems to effect the post transcriptional and post-translational modifications required for the expression of complex heterologous proteins, carried out only by the eukaryotic systems (Glick and Pasternak, 1994).

Therefore, a possible solution was pursued in the transformation of complex eukaryotic systems which could ensure at the same time the production of active proteins and the utilization of inexpensive processes. (Watson et al. 1992).

In particular, plants possess the required potential, and their capacity of functioning as bioreactors for the production of complex proteins (plants are highly efficient in this type of processes, ensuring a high degree of expression), in a cost-effective way (plant cultivation is relatively inexpensive) and with a high yield (each single harvest can yield high amounts of proteins) was proved (Fraley and Schell, 1991).

Further, very many plants satisfy the important requirement of the non-allergenicity needed for the production systems of recombinant proteins of pharmacological or alimentary interest. In fact, the organisms used in those productions must belong to the GRAS (Generally Recognized As Safe) organism category, i.e. organisms that having been used by man for a long time, are considered safe for man and for the ecosystem as well. Obviously, plants such as Leguminosae, cereals, tobacco, horticultural plants in general and fruit trees, satisfy this requirement in nature. Among leguminosae, Soya is a basic food in the diet of many populations mostly of the Third World Countries, but recently in European Countries as well. In fact, Soya-derived compounds constitute ingredients that are present in a vast number of food products, such as e.g., lecithin and seed oil, while the seeds of this Leguminosa yield a flour that is employed in various food like soybean milk containing approximately the 8% thereof.

Therefore plants, while being the raw material from which the product can be extracted according to conventional processes, at the same time constitute an alternative to the conventional production. In fact, they can be used as functional foods, i.e. foods genetically modified so as to be enriched from a nutritional point of view, and in case assuming important properties as a natural drug.

Thus the step of the protein extraction from the plant has been eliminated, and the heterologous protein expression does not prelude to an extraction and purification thereof, steps that account for most of the production cost of a drug, but simply enriches a vegetable nutriment, which thus becomes a nutriceutical, i.e. a nutriment having a pharmaceutical value.

This is the reason for the research efforts aimed at generating genetically modified plants, optimized for the above-mentioned applications.

However, to date the evaluation of the heterologous expression capacity typical of various plant species was exclusively performed under laboratory conditions, or anyhow on relatively limited surfaces in hothouse.

For instance, expression in plants of enkephalin and human serum albumin, as well as of mice monoclonal antibodies was studied (Watson et al., 1992). More recently, always referring to proteins relevant from a pharmacological point of view, two additional human proteins of therapeutic importance, i.e. active interleukin-6 and C protein (a serum anticoagulant), were successfully expressed in tobacco. In all these cases the model plant on which the functionality of the prepared gene was tested is tobacco, whereas usually the plant finally selected for production is a leguminosa, whose seed content in storage proteins is high.

These experiments proved that often the expression levels of the heterologous protein in the vegetal bioreactors do not reach high enough levels to meet the commercial demands, and that anyhow it can be improved applying new information on the plant gene control. Specifically, it was demonstrated that the level of produced recombinant protein has to reach more than 1% of the total protein amount in order to become economically significant, a level obviously not achieved by the simple introduction of the heterologous gene, whose expression therefore needs to be maximized.

In relation to the vegetal cell biology, in order to maximize the level of the in plant expression, an action on various levels is necessary: increase of genic transcription, increase of transcript stability and of the translation process yield. Moreover, it is further necessary to fix the inserted gene and to minimize the risk of the occurrence of silencing or of genic inactivation. All these factors are crucial in assessing the in plant expression level of the heterologous gene, that, as afore stated, apart from some exceptions usually settles at rather low levels (Owen and Pen, 1996).

Among all these, the most crucial factor, together with the transcription level depending on the preferential presence of certain co-dons, would seem to be the stability of the recombinant protein in the heterologous host, as the likely probable cause of its easy elimination. The relative instability might be the consequence, on one hand of the inability of the translated heterologous protein to assume a stable structural conformation, on the other hand of the ultrastructural compartment in which it is directed after the translation, where the presence of proteases and of particular pH values determine its degradation.

Accordingly, it is therefore important both to provide the modification of the heterologous sequences in order to ensure the codon optimization and to carry out a careful selection of the targeting sequences, capable of directing the translated protein into preferential ultrastructural compartments, as i.e. the seed storage tissue, capable of ensuring the stability of the product. Concerning the latter issue, the best strategy of action in this sense, is that of providing the maintenance of the endogenous signal sequences of the plant selected for the final production. In fact, the adoption of these sequences prevents the alteration of the cell internal balance, consequence of the unavoidable random accumulation of exogenous proteins that would take place in their absence. In this regard, the fact that the ultrastructural compartments have different characteristics in the cells of the various tissues has to be taken into account.

For instance, the heterologous proteins accumulated together with the storage proteins of the seeds in the transgenic plants, are more stable as compared with those of the vegetative organs (Owen and Pen, 1996). Probably, the reason of such different stability can be found in the different protease activities recorded in the vacuoles of the leaf meristem cells, with respect to those observed in the vacuoles of the seed. It is therefore understandable how research efforts are aimed at the generation of transgenic plants in which the heterologous protein be preferably expressed in the seed (Owen and Pen, 1996).

Furthermore, overall the seed constitutes the vegetal organ most used by man for its ease of conservation and, obviously, for its caloric and protein contribution. The seed consists of the plant embryo enveloped by storage tissues that provide energy and nitrogen during germination. Usually the storage tissue function is mainly effected by the endosperm, but in Leguminosae, as e.g. Soya, the cotyledons develop remarkably, and acquire this function.

The storage function for the nitrogen component is carried out by particular proteins accumulated in the protein bodies, inside compartments in the endocellular membrane systems. The amount of proteins in the seed varies from about 10-15% in cereals to about 25-35% in Leguminosae, therefore seeds are an important protein source in the human diet (Shewry et al., 1995).

In order to exploit the expression system of the seed storage proteins, first of all it has to be considered that the storage proteins of all plants have some functional and physiological common characteristics: their synthesis is controlled during the seed ripening according to the nutritional needs, and they are stored in protein bodies. In particular, the Leguminosae storage proteins are divided in two classes: globulins and lectins. Globulins are the most widespread storage proteins, present not only in leguminosa but in monocotyledons and in other dicotyledons as well. The globulin class in turn is subdivided into two subclasses: legumins (11S hexameric proteins) and vicilins (7S trimeric proteins). Also β-conglycinine and basic 7S globulin, whose regulation elements were used to perform tissue-specific expression in seed (Shewry et al., 1995) belong to the vicilin subclass, but whereas the former was studied in detail, no detailed information is available on the basic globulin functioning.

β-conglycinine is a storage protein of the Soya seed (*Glycine max*.), consisting of three different subunits, α, α', β that interact non-covalently to form a trimer complex. The subunits are coded by a multigene family of 15 genes grouped in six nuclear DNA regions, whose expression is strictly regulated so as to be modulated during the plant life (Harada et at. 1989). Control is tissue-specific as well as stage-specific. In fact, the expression of each subunit is activated at high levels at the moment of embryo development, from the heart shaped phase until complete ripening, whereas it is repressed before the dormancy phase.

Moreover, expression occurs exclusively on specific plant zones, like cotyledons, according to an expression pattern that varies in the course of their ripening; at first it is activated on the outer cotyledon area, then a wave distribution from the outside to the inside is observed and lastly it turns out to be uniformly spread over the entire cotyledon tissue. However, during the heart shaped phase (18 days after pollination), the gene encoding the β-conglycinine also expresses itself in the embryonal axis, whereas it does not express in endosperm, tegmen and in already differentiated tissues (Perez-Grau and Goldberg, 1989). The same behavior also occurs in the seed of transgenic plants belonging to other families, as e.g., tobacco, proving the same control mechanism to be functional in solanaceae as well (Naito et al. 1988; Perez-Grau and Goldberg, 1989).

The regulation of subunits α/α' and β genic expression occur at a transcriptional as well as a post-transcriptional level (Harada et al., 1989). α' subunit, of 76 Kd, with a 2.5 Kb mRNA, is accumulated more precociously and in a larger amount as compared to β subunit. This behavior is due to the greater strength of the α' subunit due to the presence of an enhancer region, absent in β, and of a sequence stabilizing the α' transcript, it also absent in β (probably a 560 pb region in the first exon of the α' transcript) (Harada et al., 1989). This difference in expression has also been highlighted in transformed tobacco plants (Bray et al., 1987).

In contrast with the α' subunit, the expression level of the β subunit, is also influenced by abiotic stresses, methionine level in the ground and presence of ABA. The base elements involved in gene control at transcriptional level for the α' subunit are clustered in the 905 pb region at 5' of the transcription start site, region called URS (Upstream Regulatory Sequence). Inside this area specific sequences functioning as site-specific enhancers have been detected. Among these, the legumin boxes (5'-CATGCAC.3' and 5'-CATGCAT-3'), elements that are found in many other genes encoding seed-specific proteins, in particular in legumes. A coordinated action of the two sequences determines a 10-fold increase of the seed gene expression level. The regulation by the above elements seems to be of a positive kind (Chamberland et al. 1992), however so far trans-elements specifically interacting in those sites have not yet been found. Site-specific expression also requires the coordinated action of elements operating in cis, not yet characterized, located in the region at 5' of the legumin boxes and at 3' of the promoter (Chamberland et al., 1992). Probably the region at 5' includes a negative control site, specific for a nuclear factor present only in non-seed tissues. This factor would determine gene expression in embryonal tissues only. The importance of CAAT and TATA sequences in the control of site-specificity has also been proved.

Four Soya nuclear factors that interact with specific sequences present in the α' and β URS of the gene have been identified as well. Two of those embryonal factors, SEF3 and SEF4, bind to sites inside the enhancer region (from −257 to −79). SEF3 binds to the middle of the sequence 5'-AAC CCA . . . AACCCA-3', present exclusively in the gene encoding the α' subunit. Accumulation and degradation of this protein (SEF3) is paralleled by accumulation and degradation of α' mRNA, supporting the hypothesis that SEF3 be involved in the control of α' expression. As compared to SEF3, SEF4 is present in a lesser amount, has many recognition sites (5'-A/GTTTTTA/G-3') in α', but mostly in β. The presence of this factor is correlated to the regulation of β expression (Lessard et al., 1991). Deletion and site-specific mutagenesis experiments have proved that the sole action of these factors does not affect the site-specificity nor the expression level, coordination with the activity of the other regulatory elements being necessary. However, on the basis of the homology with light-induced proteins, these proteins are supposed to have a regulating role only under certain conditions (Fujiwara and Beachy, 1994).

Embryonal factors with a behavior similar to the SEF3, as verified in gel shift experiments, have been found in tobacco as well (Lessard et al., 1991). This and other data obtained with GUS activity assays under control of Soya α' promoter prove that the site- and stage-specific control mechanism is conserved (Lessard et al, 1991; Riggs et al., 1989). It has also been hypothesized that tobacco trans factors binding to 35SCaMV promoter may also interact with the legumin boxes (Katagiri et al., 1989). None of the afore mentioned factors appears to be directly responsible of the time regulation, and no NRS-like factor has been found possessing a negative control as in the case of bean (Bustos et al. 1991).

More recent studies, concerning some legumins and vicilins in *Vicia Faba*, contradict some generalizations on the regulation of the storage proteins expression in seeds (Wobus et al., 1995), showing that expression of genes of B4 and LeB4 *Vicia Faba* legumins is not limited to embryonal tissues, nor are they temporally restricted to the cell expansion phase in embryogenesis. Proteins are stored for short periods of time and then degraded in all embryonal tissues, suspensor and endosperm included, within well-defined developmental stages. This is so probably in order to allow an uninterrupted supply to the embryo of compounds having a high C and N content during all the growth and differentiation stages. Therefore, this data allow to hypothesize that the seed proteins expression be also controlled metabolically, and not merely at a developmental stages level. The possible relationship existing between storage proteins accumulation and carbohydrate metabolism (soluble glycid level) is presently being investigated. Since all classes of seed storage proteins share a similar behavior in the different species, this data require a careful evaluation of the behavior, in terms of expression, also for the Soya proteins β-conglycinine and 7S basic globulin. Data resulting from the study, which the present invention is based on, clearly show the tissutal specificity of the expression of the structural portion of lactoferrin under control of both the promoters. Instead, the activation phase was at the present not investigated in detail as the sole capability of total seed accumulation was of interest. Specifically concerning the 7S basic globulin, it is a storage protein of the Soya seed, with a high methionine and cysteine content. Alike β-conglycinine, also 7S basic globulin (Bg) is stored in seed in large amounts (3% of seed total proteins). It consists of two subunits, one of 27 KDa, the other of 16 KDa encoded by the same mRNA, linked by disulfide bridges. Bg is synthesized as sole precursor polypeptide consisting of a putative peptide signal and of two subunits. This polypeptide is processed to yield the mature dimeric protein. In the genome about four copies of the Bg gene are present (Watanabe and Hirano, 1994).

This protein is mainly located in the seed embryonal tissues and its expression pattern is unusual for a storage protein. In fact, a portion of Bg is accumulated in the intercellular spaces of the cotyledon parenchyma (Nishizawa et al., 1994), whereas at an intracellular level it is stored in protein bodies on the middle lamella of cell wall and in the plasma membrane (Watanabe and Hirano, 1994). This location suggests that the Bg is not a mere storage protein, having other functions as well. More accurate data on Bg location and expression period in Soya are not available. It has never been verified whether the site- and time-specific expression mechanism be preserved in other transformed vegetal species (like tobacco). To this end, reference is made to general data on storage proteins and to studies on Bg homologues in lupine (conglutyn γ), with which it has a high sequence homology. This protein is stored only in lupine embryonal tissues (cotyledons and embryonal axis) 40 days after blooming. It has not been detected in other tissues such as leaves and sprouts. In seeds of transgenic tobacco, the conglutyn γ gene is increasingly expressed from the 15th to the 20th day after blooming until the 40th, then begins to decrease (Ilgoutz et al., 1997).

One of the peculiar features of the Bg is that it is secreted in large amount from Soya seeds soaked in water at 40-60° C. It is uncertain whether the secreted proteins are neosynthetized after heat-treatment, or instead are the proteins already present to be secreted. Since a post-heating increase in specific mRNA has been highlighted, it is assumed that the Bg is actually synthesized as a consequence of the thermal shock (Hirano et al., 1989).

Not much is known on the regulation mechanism of the expression of the gene encoding the Bg protein, nevertheless sequences in the promoter region involved in the gene regulation have been identified. Besides the CAAT and TATA box sequences, respectively located at −116 and −25 with respect to the transcription start site, three regulatory elements similar to thermo-specific sequence enhancers present at the non transcribed 5' region of genes in other organisms, have been detected. These heat shock elements (HSE) consist of two 5 pb conserved units: 5'-NGAAN-3' and 5'-NTTCN-3'. In the thermoregulated promoter of the Soya heat-shock protein, the enhancer elements, observed also in Bg as well, cooperate synergistically with three CCAAT box sequences located upstream thus increasing gene expression; these putative sequences are present also in the bg promoter.

Sequences responsible of the site- and time-specificity expression were not identified.

The interest for this protein derives from the fact that it is accumulated in high amounts in the Soya seed (3% of total proteins) and therefore has a strong seed-specific promoter which can ensure a high level of expression of the gene it controls. Moreover, it is known that the regulation mechanism of this protein is different from that of the other storage proteins of Soya seed but the details are not known. However, studies on the promoter and on its site- and time-specific activation mechanism have never been carried out using reporter genes in transgenic plants.

Both Bg and CONG, as storage proteins, are synthesized exclusively in the seed tissue and are stored in large amounts in cells constituting this organ, inside specific compartments. Concerning the post-transcriptional and above all the post translational regulation level, it runs through the mechanisms of intracellular transport and of protein compartmentalization, which are to date to be clarified in many aspects.

In fact, those mechanisms involve all processes influencing the concentration, retention and distribution of the proteins in the endomembrane system (Okita, 1996).

However, general principles of protein targeting do exist, valid for all plant species.

1. Targeting information are contained in the proteins themselves, as discrete signals. Those signals are intercepted by specific recognition signals such as receptors or simple interactions with membrane lipids.

2. Different types of signals do exist (topogenic sequences) each with a specific function. Among them there are signal sequences that start the protein translocation across specific endomembranes and interact with receptors/translocators facilitating the unidirectional transfer. Then there are stop and retention sequences that block the transfer to the membrane or to the inside of the compartment. Selection sequences target proteins to the various cellular compartments. All those elements can be of a sequential type, i.e. localized in the N-terminus, central or C-terminus portion of the protein, or conformational, i.e. consisting of amino acids which although nonsequential, are yet adjacent in the native protein conformation. Moreover, there may be various signals simultaneously, and they can be modified or activated (e.g. by phosphorylation). After transfer the signal is often deleted using specific cleavage sites for endogenous proteases.

mRNA accumulation in a particular region also influences the protein location. Soya seed storage proteins, globulins as well as lectins, are stored in storage vacuoles. In fact, several types of vacuoles do exist. Some of them, besides having the function of maintaining the turgor pressure and of regulating ion, sugars and amino acid release, also constitute the depository of storage and defense proteins. The specific signal sequence for targeting to the vacuole has not been identified yet, apart from some plant species (Kermode, 1996). Probably, one or more surface regions of the correctly conformed protein are recognized by the selection mechanism. Plant cells possess the unique feature of accumulating storage proteins in the protein bodies, whereas in animals similar inclusion bodies are formed only when an excess of protein synthesis occurs. Therefore, the latter protein bodies consist of unmuddled accumulation of conformationally incorrect or partially processed proteins. The formation and organization process of the protein bodies in plants remains unclear, although it is known that it consists of a series of ordered events (Okita, 1996). Globulins are proteins with an acidic isoelectric point (pI), accordingly they are translocated in the endoplasmic reticulum (ER) and in the Golgi complex as soluble proteins. As soon as they reach the vacuoles, due to their low pH or possibly to the processing and assembly, these proteins precipitate forming particled aggregates that will thereafter originate the protein bodies (Kermode, 1996).

In leguminosae, different storage proteins are accumulated in the same protein bodies with no spatial segregation. In other plant species the protein bodies form in the ER and are then absorbed in vacuoles by autophagocytosis (Kermode, 1996).

This general pattern is well-grounded for β-conglycinine as well, though the specific vacuole targeting sequence have not been identified for this protein. Instead, the β-conglycinine binding with a BIP-homologous protein has been observed. This protein functions as chaperonine and, just like other proteins in different plant species, can have the role of retaining β-conglycinine in the ER until its correct conformation is reached (Galili et al., 1993; Shewry et al., 1995; Kermode, 1996; Fontes et al., 1996). As for 7S basic globulin, available information is scarce. It is known that it is located in protein bodies on the middle lamella of cell wall and in plasma membrane and not in vacuoles (Watanabe, 1994). For this reason, its mechanism of division into compartments is hypothesized to be different from that of β-conglycinine. However, it is known that even wall-located proteins follow the same transport pathway of the vacuole proteins, i.e. are translated in the ER, then transported to Golgi and lastly secreted to the outside or inserted in the membrane by vesicular traffic.

However, storage proteins expression in heterologous hosts shows that the compartmentalization mechanism is universal. In transgenic plants the seed vacuole storage proteins are correctly targeted. Nevertheless, sometimes transport can be inefficient, especially in vegetative organs with respect to seeds. In tobacco, leguminose storage proteins are correctly targeted to vacuoles both in seeds and in leaves, yet in leaves there is a lower accumulation level. This is so because a difference exists in the transportation efficiency or because of a different processing rate (different proteases or higher instability). Hence, it can be understood how seed-specific in plant production of a heterologous human protein is a complex mechanism, so that the preliminary verifying of the functioning and efficiency of the expression system, as constructed in a model host organism, constitutes an important step.

It has been seen how tobacco is one of the most widely used plants to this end. Its preferential use in assays derives from the fact that it is one of the better known plants, both in a genetic and in a biological and physiological respect. This, together with the ease of effecting the genetic transformation and the shortness of vegetative cycle, made it become an important model for biotechnological experiments, a model whose transformation specific systems and micropropagation conditions are now better known. Additionally, tobacco possesses the further advantage of a near-complete extensibility of the obtained results to several other plant species, consequence of the high conservation rate of genic control mechanisms, that precisely proved to be usually highly conserved in other plant species, and in particular in leguminosae. Therefore it is particularly suitable for the study of the promoters taken out therefrom, and in particular of their capacity of allowing a gene of interest to be expressed in a controlled way in a transformed plant. Genes of interest are usually those encoding proteins suitable in a pharmaceutical or alimentary field. Accordingly, a heterologous gene of interest for this kind of application is that of the human lactoferrin, a protein belonging to the transferrin family, and as such capable to stably and reversibly bind two iron ions.

In fact, by virtue of its biological functions lactoferrin turns out to be interesting from a nutritional as well as from a pharmacological point of view. It is present in human milk and has a fundamental role in neonatal feeding, as a matter of fact several biological functions have been attributed to this protein, among which a bactericidal and bacteriostatic activity against a wide range of pathogenic microorganisms and the capacity of increasing iron absorption at the intestinal level (Lonnerdal and Iyer, 1995; Hambraeus and Lonnerdal, 1993). Moreover it promotes cellular growth, controls myelopoiesis and is capable of modulating the inflammatory response (Lonnerdal and Iyer, 1995; Oguchi et al. 1995; Penco et al. 1995).

Therefore, at first, attempts to research in milk of other mammals a protein capable of binding iron and possessing the same properties were carried out.

It has been observed that milk of all mammals contains two types of iron-binding proteins, present in different ratios: transferrin, identical to serum transferrin, and lactoferrin. Human milk has a particularly high lactoferrin content, in fact its concentration in colostrum is of 5-10 mg/ml, although it decreases during lactation to about 1 mg/ml in ripe milk (Hambraeus and Lonnerdal, 1993). However, the amount of lactoferrin is much lower in milk of other animal species, like goat, horse, pig and mouse, In cow's milk for instance its concentration is of about 0.1 mg/ml. In some species such as rabbit, rat and dog, lactoferrin is absent, the prevailing iron-binding protein being instead transferrin.

Further, lactoferrin (LF) produced by other non-human mammal species, assumes in each of them different structural characteristics, and therefore different properties.

Human lactoferrin (LFU) is a 78 KDa monomer glycoprotein, with a bilobate structure. There is a high degree of homology between the N-terminus domain and the C-terminus one, both at the amino acidic sequence (37%) and at the tridimensional structure level. The tridimensional structure has been described in detail by X-ray crystallography (Lonnerdal and Iyer, 1995). The gene encoding LFU has been cloned and sequenced. Genic control mechanisms at a transcriptional and translational level and estrogens and iron role in those mechanisms are also known (Liu et al, 1991). The mature protein consists of a 692 aa polypeptidic chain with a 8.8-9 pI. It contains 16 disulfide bridges and shows some resistance to proteolysis (Lommerdal, 1995), has three glycanic polyacetylactosaminic chains bound with N-glycosidic bonds to the amino acidic residues Asn233, Asn476 and Asn545 and the molecular weight of the glycosilated protein is 82 KDa.

One of the most important differences existing among lactoferrins (LFs) present in the various animal species is precisely the glycosidic chain composition. In fact, unlike human LF, bovine LF contains α-1,3 galactosidic residues and glycans of oligomannosidic type; the role of the glycosidic chains has not been defined yet, however it is possible that glycans protect LFU against attacks from proteolytic enzymes. Each of the two LFU domains is capable of binding tightly, yet reversibly to a ferric ion and at the same time to a carbonate or bicarbonate ion molecule (Hambraeus and Lonnerdal, 1993). Iron binding sites in human milk lactoferrin are not completely saturated, but only at 6-8% of their capacity (Stowell et al., 1991).

In recent years, a series of studies aimed at understanding the mechanisms of action and the relation between molecular structure and function of this protein have been carried out. The strategy adopted was that of studying LF molecules structurally altered by site-specific mutagenesis. Accordingly, expression systems of LFU recombinants producing in a simple and inexpensive way a protein as identical as possible to the one purified from human milk were carried out.

However, all heterologous hosts used so far for the LFU recombinant are eukaryotes, as, it being a complex glycoprotein, requires a sophisticated processing apparatus.

In 1991 Stowell et al. cloned the LFU gene in cultured neonate hamster renal cells. An inducible $Zn^{2+}$-promoter and the secretion signal of a hamster endogenous protein were used to maximize expression. Concentration of LFU recombinant secreted in the culture medium was of about 20 mg/l, sufficient for crystallization and therefore for structural studies. Characterization revealed that it has the same molecular mass of native LFU maintaining intact the iron-binding site. It only differs from human milk LFU in the glycosidic chains and N-terminus sequence, but these do not influence folding. Such an expression system is highly expensive and not suitable for the production of the amounts of proteins required at an industrial level.

Then LFU was expressed in transgenic mice's milk. In this case the entire animal rather than the cultured cells was transformed, using the regulation sequence of the bovine gene α-S1 caseine. It was shown that LFU mRNA is exclusively expressed in female mammary gland during lactation. In milk the protein reaches a 0.1-36 µg/l concentration. Recently this LFU recombinant has been characterized (Nuijens, 1997), and it has been observed that it has the same molecular mass, N-terminus sequence and immunoreactivity of native LFU. It also maintains the capacity of releasing iron at acidic pH and the bond to bacterial lipopolysaccharides. Also in this case, glycosilation, as well as in vivo bactericidal and antiinflammatory action, are different from the ones in native LFU.

Indeed, a highly significant production system of recombinant LFU is that carried out in *Aspergillus awamori* (Ward et al, 1995). This method, which is patented, yields commercial amounts of recombinant LFU (2 g/l). In order to maximize expression LFU is produced as a fusion protein with part of the structural gene, regulation sequence and secretion signal in the culture medium of the glucomylase. The fusion polypeptide is processed to yield mature LFU by an endogenous peptidase. Glucoamylase is an *Aspergillus* protein expressed in high amounts.

An alternative eukaryotic host is the one used by Mitra and coworkers in 1994. They have transformed tobacco cells in suspension. In the transgenic calluses a protein much shorter than the native LFU and therefore found to be unstable is produced in small amounts. Recombinant LFU shows activity against phytopathogenic bacteria, e.g., *Xantomonas campestri*, *Pseudomonas syringae* and others. In the above-mentioned study the obtaining of entire and fertile plants is not reported.

Recently LFU was also produced in culture in insect cells, using Baculovirus as expression system (Salmon et al., 1997). This is a highly powerful expression system yielding a recombinant protein identical to the native one, apart from the glycosilation level. Nevertheless it maintains the binding with the specific receptors.

All the above reported expression systems allow to obtain an amount of protein sufficing for functional studies, and in some cases (Aspergillus) for commercial uses as well. In the latter case however, safe use of the purified protein, e.g. in milk substitutes for neonates, requires an excessive purification in order to ensure the absence of immunogenic or allergenic substances. However, transgenic plants have never been used to this end, nor products directly suitable in human nutrition have been ever yielded, for instance by the recombinant LFU expression in alimentary plants.

SUMMARY OF THE INVENTION

The present invention relates to a general system of tissue-specific, and in particular seed-specific, accumulation of heterologous proteins, designed and carried out with the object of maximizing the production while preventing the degradation thereof, by using leader sequences and promoters of Bg and β conglycinine genes. To this end, the structural part of the selected gene may encode proteins having an enzymatic activity, used in human therapy or in industrial processes, or proteins with a general (lactoferrin) or specific (antibodies or antigens) pharmacological activity, or antibody proteins for phytopurification or for the elimination of mycotoxins present in foods.

The present invention also relates in particular to a system that, enabling the in plant tissue-specific expression of the human lactoferrin gene, provides an important solution to the problem of the production of this protein. This system in fact determines the production of plants capable of expressing relatively high amounts of this protein that, in the preferred embodiment providing the expression of a synthetic gene designed by the inventors so as to maximize its in plant expression, reaches industrially relevant levels. Moreover, such transgenic plants allow to avoid the costly product purification processes, as they can be used as nutraceuticals, and therefore being directly intaken as alimentary products. Accordingly, also the use for the production of protein flours or of protein extracts yielded from tissues, and specifically from seeds of the afore mentioned transgenic plants, for the production of functional foods or special preparations for children is possible.

The protein accumulation in the seed further allows to significantly increase the iron content of the same, or of the flours derived therefrom. Accordingly this system allows the obtaining of foods which, having a twofold iron content with respect to analogous product, can be also used for supplying this micronutrient's deficiency through a normal alimentation.

These plants can anyhow be used also for human lactoferrin purification, by conventional methods based on chromatography techniques.

This expression system further provides the use of new recombinant vectors, constructed by testing the effect of various leader sequences and processing sites of the mature protein, enabling the production of any protein of interest and in particular of lactoferrin or of fragments derived thereof, with a tissue-specific protein accumulation, in plants belonging to different families among which leguminosae, cereals, solanaceae, fruit-bearing plants and horticultural produce in general. In particular they are structured so as to have the following functionally linked components: (a) a promoter; (b) a signal sequence; (c) a nucleotide sequence optimized for in plant expression and corresponding to the amino acidic sequence of the entire human lactoferrin or to fragments thereof; (d) a polyadenylation signal.

In particular the case concerning plasmid is considered, and wherein regulation elements and signal sequences used are those belonging to two genes encoding storage proteins that are very common in Soya seeds, i.e. a β-conglycinine and a 7S basic globulin, isolated and cloned from the Richland soya variety. They can be used to transform plant cells both by the *Agrobacterium* method and by direct physical methods (Gelvin and Schilperoort, 1995; DuPont Biolistic Manual, DuPont). The vegetal transformed cells are hence selected with the selection agent provided for the purpose and induced to form entire fertile plants capable of forming seeds, in turn capable of expressing the gene for lactoferrin, and accumulating it as storage protein.

This result was obtained by designing and synthesizing an artificial gene encoding the same amino acidic sequence of the natural human gene, but having sequence mutations such that codons most frequently used by the human cell are replaced with those most frequently used by the vegetal cell. This result yielded the change of the 31% of the codons in the original gene (see table 1). The remarkable production of human lactoferrin detected in the various plants transformed with the synthetic gene, with yields going from 1% to 1.8% of the seed total storage proteins, but not in plants having the natural gene, proved the in plant functionality thereof. Furthermore on the basis of such sequence, which allows the efficient expression of the human lactoferrin in any vegetal cell, a person skilled in the art can derive the specific sequence expressed with a higher efficiency in each single vegetal species, by the simple application of the common general knowledge.

Concerning all the above disclosed, object of the present invention is a polynucleotide encoding human lactoferrin, characterized in that it has a sequence totally or partially corresponding to the sequence reported as SEQ ID NO:1, or to a sequence biologically equivalent thereof and in that said sequence is optimized for in plant expression, and in particular the case wherein said polynucleotide has fused to the 5'-terminus end a sequence selected from the group comprising the sequences shown as SEQ ID NO: 13 and NO: 14. A particular case of sequence partially corresponding to the SEQ ID NO:1 is given by a sequence corresponding to one or more fragments of said sequence.

Object of the present invention is also the human lactoferrin protein, obtained from the expression of the afore mentioned sequences.

A further object of the present invention is a recombinant DNA vector, in particular a plasmid, comprising at least one sequence of a gene of interest, in particular the gene encoding the complete human lactoferrin, specifically a sequence totally or partially corresponding to the SEQ ID NO:1, operatively linked to regulation elements enabling the tissue-specific expression of said gene. A special case is the one where such regulation elements consist of an expression cassette for plants allowing tissue-specific expression of said gene.

Further cases of interest are those wherein the expression cassette for plants are constituted by the regulation elements of the protein 7S basic globulin, and in particular when among said regulation elements there is the sequence reported as SEQ ID NO:21, or the regulation elements of the β-conglycinine protein, and in particular when among said regulation elements there is the sequence reported as SEQ ID NO:22, the case wherein the sequence of the gene encoding complete or partial human lactoferrin is operatively linked, or even fused, to a leader sequence, and the case wherein such leader sequence is selected from the group comprising sequences SEQ ID NO: 13 and NO: 14.

Of particular importance is the case wherein such plasmid is selected in the group comprising vectors pBI, pGEM or pUC.

A further object of the present invention is constituted by the transformation process of vegetal cells wherein the transformation is effected with one of the above-mentioned vectors, the transgenic vegetal cells can be obtained through transformation of wild type vegetal cells with at least one of the same vectors, and by the cells that anyhow contain a gene of interest, or portions thereof, and in particular the gene encoding human lactoferrin operatively linked in an expression cassette, enabling the tissue specific expression of the gene itself, in particular that of the gene encoding 7S basic globulin and that of the gene encoding β-conglycinine.

A further object of the present invention is constituted by cellular aggregates and in particular calluses characterized in that they are obtainable by the aforesaid cells.

A further object of the present invention is also the transgenic plants obtainable from the aforesaid cells with conventional techniques, or anyhow containing a gene of interest and in particular the gene encoding human lactoferrin, specifically the one with a sequence corresponding totally or partially to SEQ ID NO:1, operatively linked in an expression cassette enabling the tissue specific expression of the gene itself. (SEQ ID NO:23 shows the amino-acid sequence that corresponds to the nucleotide sequence of SEQ ID NO:1.)

Of particular relevance is the case wherein such transgenic plants are selected from the group comprising solanaceae, cereals, leguminosae, horticultural produce and fruit-bearing plants in general, in particular Soya, tobacco and rice, wherein the gene encoding lactoferrin is specifically expressed in the storage tissues or in the fruit. A further object of the present invention is the use of such transgenic plants as nutriceuticals.

A further object of the present invention is constituted by the production processes of functional foods containing proteins produced by the aforesaid transgenic plants, of vegetal milks, starting from natural and/or concentrated proteins deriving from the above-mentioned plants, and anyhow any human lactoferrin production process, characterized in that it utilizes the aforesaid plants.

Lastly, object of the present invention is also the human lactoferrin obtained from the aforesaid transgenic plants.

The invention will be better described with the aid of the annexed figures.

DESCRIPTION OF THE FIGURES

FIG. 6 shows the comparison between the published sequence of gene CONG promoter region (SEQ ID NO:24) and the one cloned in plasmid pGEM-PCONG (SEQ ID NO:25).

In contrast, box (B) shows the construction of a plasmid containing the synthetic gene reported in the sequence list as SEQ ID NO: 1 and cloned in plasmid pBI101 fused to promoter PCONG and in open reading frame with the β-conglycinine leader.

Figure 10:
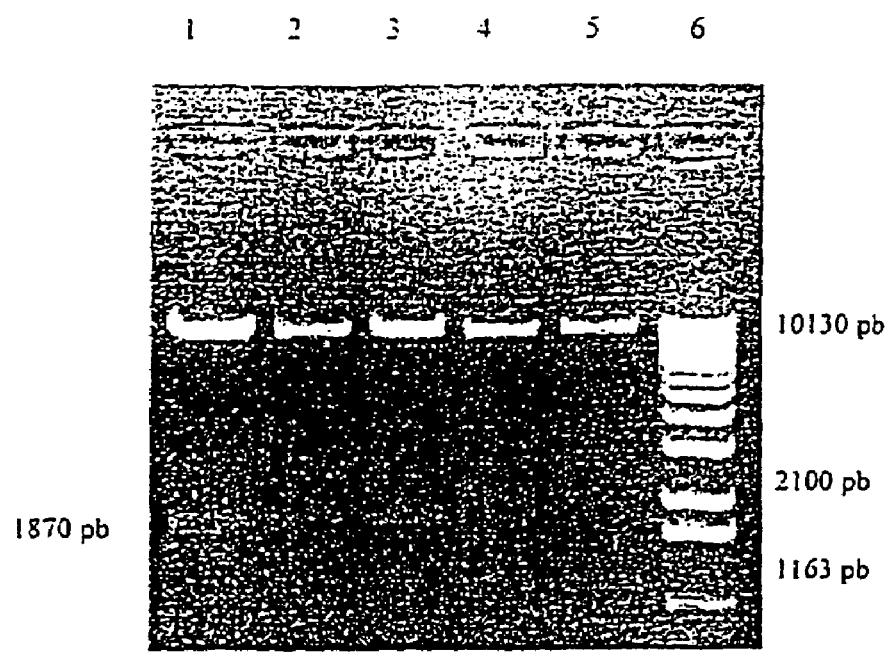

FIG. 10 shows electrophoretic analysis of the restriction of various clones of plasmid pBI-PCONG-LFU with enzymes Xba I, BamH I, Sac I; samples 4 and 5 test positive. In position 6 molecular weight marker Ladder 1 Kb is present.

Figure 11:

FIG. 11 shows electrophoretic analysis of the restriction of two clones of plasmid pBI-PCONG-LFU with enzymes Sal I (lanes 1 and 2) and with Xba I and Sac I (lanes 4 and 5); Both samples tested positive. Samples 3 and 6 represent the positive controls, i.e. pGEM-PCONG-LFU digested with Sal I, Xba I and Sac I respectively.

Figure 12:
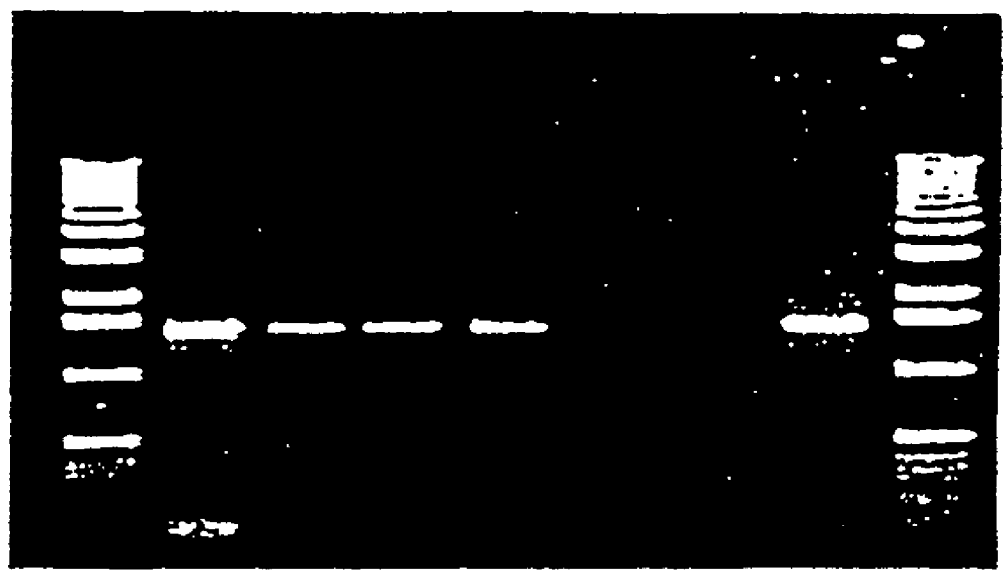

FIG. 12 shows agarose gel electrophoresis analysis of PCR products from genomic DNA extracted from various plants transformed with pBI-PGLOB-LFU, performed using primers PLT48 and PLT49 for the promoter sequence PGLOB. Positive samples 2, 3, 4 and 5 represent the band of the DNA amplified to 1500 base pairs, while samples 6, 7 and 8 represent the negative control of PCR and the positive control (pGEM-PGLOB) respectively. Molecular weight markers Ladder 1 Kb are found at 1 and 9.

Figure 13:
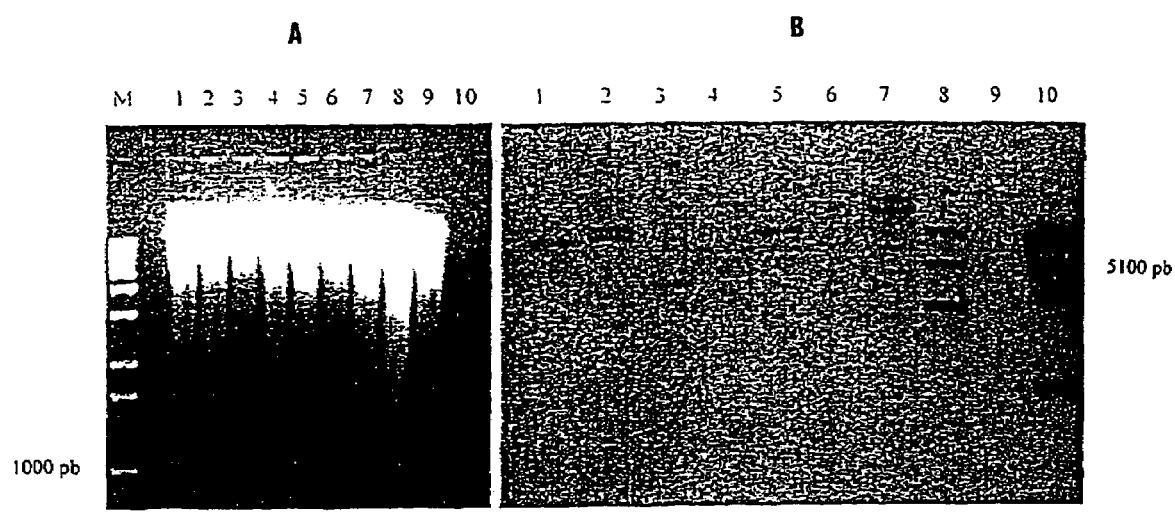

FIG. 13 shows in box (A) the agarose gel with the genomic DNA of tobacco transformed with pBI-PCONG-LFU (lanes 1-5) or with pBI-PGLOB-LFU (lanes 6-9) cut by enzyme BamH I. M is the molecular weight marker Ladder 1 Kb. Sample 10 shows the positive control pGEM-LFU, not shown in the photo for quantitative reasons. In box (B) the hybridization pattern of human LF on the genomic DNA of the same tobacco plants is shown; samples 1, 2 and 3, belonging to plants PCONG 1, PCONG 3, and PCONG 4 respectively are positive, as is the case for samples 5, 7 and 8, belonging to plants PGLOB 10, PGLOB 3 and PGLOB 4 respectively. It is evident that PGEM-LFU, the positive control (lane 10), was only partially digested as also the super-coiled plasmid forms are present.

Figure 14:
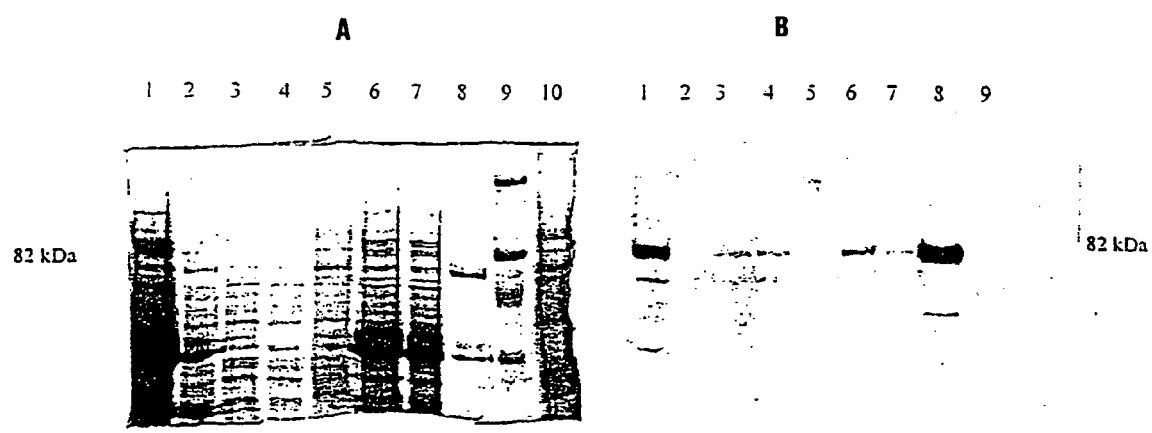

FIG. 14 shows SDS-PAGE electrophoretic analysis of proteins partially purified from seeds of the transgenic plants tested with Southern analysis of the preceding figure (A) and Western analysis of the same proteins, after transfer to a membrane, using polyclonal antibodies specific for the human lactoferrin (B). In particular, in box (A) SDS-PAGE electrophoretic analysis of total cellular proteins (30 DAP) from mature seeds of transgenic tobacco is shown. In position 2, 3, 4 and 5, 6, 7 the same samples tested positive to Southern analysis, extracted by buffer at pH 2.7 and pH 7.6 respectively, are found. Samples 8 and 10 represent the positive control (milk-extracted human lactoferrin, Sigma) and the negative control (non-transformed plant of the same variety), while in position 9 the molecular weight marker Rainbow (Amersham) is found. In box (B) autoradiography of anti-lactoferrin antibody hybridization with the same proteins transferred to DEAE-nitrocellulose membrane is shown; the sample corresponding to plant PGLOB 10, in position 2 and 5, does not yield a positive signal, although according to Southern analysis it is transformed. All other samples are positive.

Figure 9:
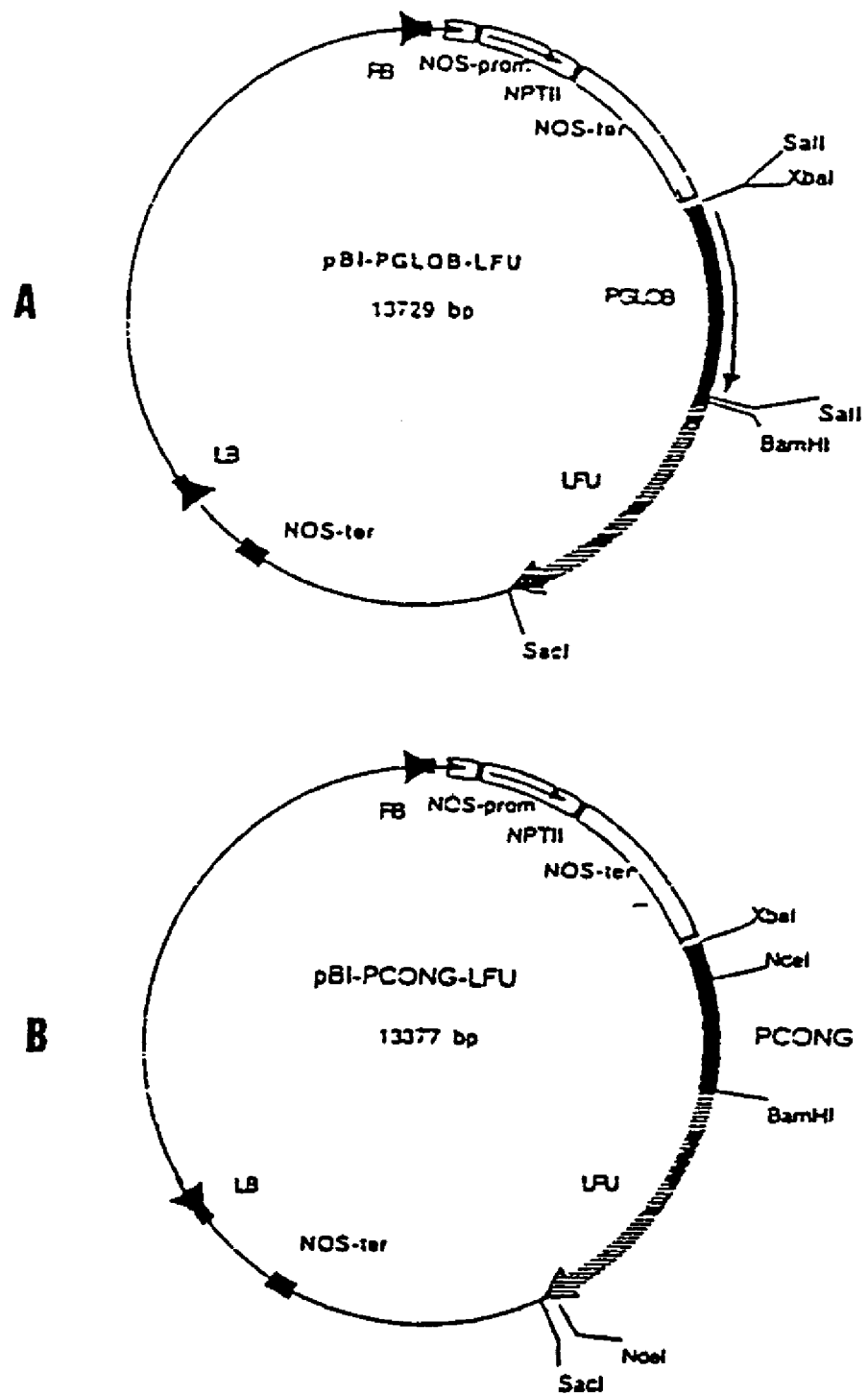
FIG. 9 shows the map of plasmids pBI-PGLOB-LFU (A) and pBI-PCONG-LFU (B) wherein the restriction sites used are highlighted. In particular, box (A) shows the construction of a plasmid containing the synthetic gene represented in the sequences list as SEQ ID NO:1 and cloned in plasmid pBI101 fused to promoter PGLOB and in Open Reading Frame with the "leader" of 7S basic globulin.
Figure 15:
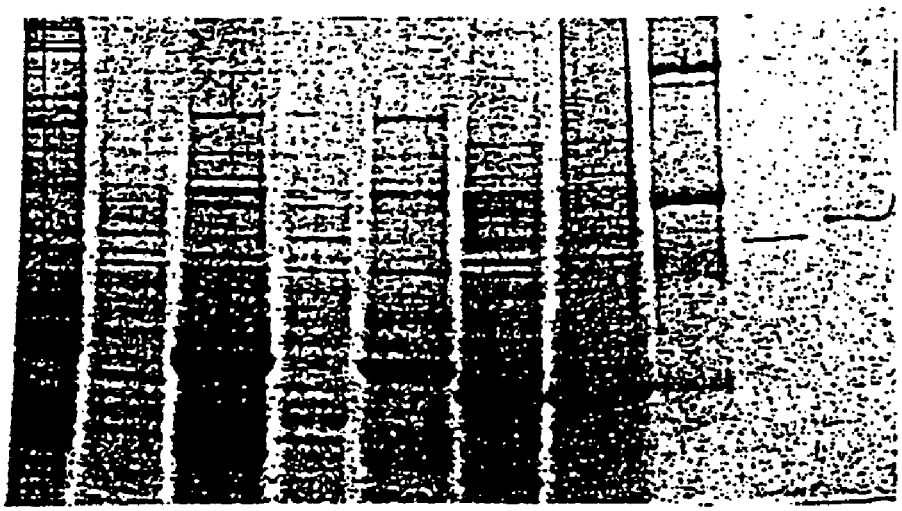
Figure 15:
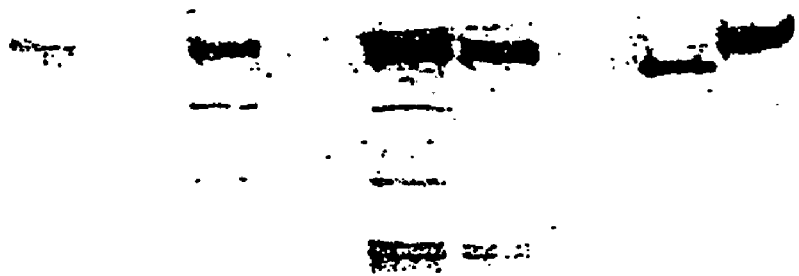

FIG. 15 shows electrophoretic analysis of raw proteins extracted from seeds and leaves of the transgenic tobacco transformed with the plasmids of which at FIG. 9. In particular, in box (A) protein coloration carried out with Coomassie blue is reported. In box (B) Western Blotting carried out with human LFU-specific antibodies on the proteins of the gel shown in box (A) after transfer to membrane is reported. In particular, in lane 1 plant PGLOB 1, with leaf-extracted proteins is reported, in lane 2 always plant PGLOB 1, with seed-extracted proteins is reported, in lane 3 plant PGLOB 3, leaf proteins, is reported, in lane 4 plant PGLOB 3, seed proteins, is reported, in lane 5 plant PCONG 105, leaf proteins, is reported, in lane 6 plant PCONG 105, seed proteins is reported, in lane 7 plant PCONG 105, seed proteins treated with N-deglycosilase F, is reported (see text), in lane 8 the molecular weight marker is reported, in lane 9 the human LFU present on the market treated with N-deglycosilase F is reported, in lane 10 LFU present on the market is reported.

Figure 16:

FIG. 16 shows Western analysis of LFU protein extracted from human milk and of recombinant protein isolated from tobacco seed, before and after N-deglycosilase F enzyme treatment. Analysis was performed with human lactoferrin specific antibodies. In lane 1 LFU extracted and purified by HPLC from seeds of plant PCONG 105 is reported; in lane 2 a protein as in 1 after a 18-hours treatment with N-deglycosilase F is reported; in lane 3 commercial LFU after a 18-hours treatment with N-deglycosilase F is reported; in lane 4 commercial LFU is reported, a diminution is apparent in the molecular weight of the two enzyme-treated samples (2 and 3).

DETAILED DESCRIPTION OF THE INVENTION

The strategy adopted for the generation of transgenic plants capable of producing human lactoferrin was developed along two directions: on the one hand, comparative analyses on plant expression systems, particularly tobacco and Soya, have been carried out, in order to have a basis for the designing of a sequence encoding human lactoferrin thereof, sequence optimized to maximize its expression in vegetals. Accordingly in the sequence designing the necessity that the required post-translational modifications for the production in the active form could be effected on the translated protein, and that, both for its conformation and due to its subcellular localization, the protein be sufficiently stable to be accumulated in relevant amounts in the transformed plants, was taken into account. This proved crucial, having ascertained after various attempts carried out in the past years the impossibility of an in plant production of human lactoferrin using constitutive expression systems (e.g. promoter 35S) as well as promoters inducible by leaves cut. Moreover, besides difficulties related to the type of promoter used, the production level and the stability of the protein were tested to be scarce and depending on a warped preferential use of the codons between the human gene and the plants.

Therefore, a plasmid vector system was developed utilizing vectors containing a newly synthesized lactoferrin gene regulated by tissue- and stage-specific promoters capable of yielding a high gene expression and of accumulating the protein in a stable and efficient way inside seed storage organs. Moreover the selection of leader sequences and the design of the fusion point between those and the structural portion of the mature protein yielded a lactoferrin protein that, in quantitative and possibly also in qualitative terms, has the same glycosilation level and the same amino terminal sequence of the native protein, which is important for some of its functional characteristics.

Concerning the synthetic gene design, all the necessary and possible triplets were modified taking into account their preferential use in the two reference plants, tobacco and Soya. In particular, data represented in table 1 were used.

TABLE 1

| CODONS | | HUMAN | SOYA | TABACCO | LFU WT | LFU SYN |
|---|---|---|---|---|---|---|
| ARG | CGA | 5.6 | 4.5 | 4.8 | 3 | 3 |
| | CGC | 11.2 | 7.5 | 3.8 | 5 | 5 |
| | CGG | 10.7 | 2.2 | 2.2 | 7 | 3 |
| | CGT | 4.6 | 7.4 | 7.7 | 4 | 8 |
| | AGA | 9.6 | 14.8 | 12.5 | 13 | 16 |
| | AGG | 10.8 | 11.3 | 12.1 | 13 | 10 |
| LEU | CTA | 6.1 | 7.0 | 7.4 | 0 | 2 |
| | CTC | 20.1 | 16.2 | 12.7 | 10 | 9 |
| | CTG | 42.1 | 10.3 | 7.1 | 28 | 8 |
| | CTT | 10.8 | 23.7 | 21.8 | 9 | 19 |
| | TTA | 5.4 | 8.4 | 10.3 | 2 | 2 |
| | TTG | 11.1 | 20.5 | 20.7 | 9 | 18 |
| SER | TCA | 9.7 | 14.7 | 15.8 | 5 | 11 |
| | TCC | 17.8 | 9.5 | 10.0 | 13 | 7 |
| | TCG | 4.1 | 4.3 | 4.3 | 2 | 2 |
| | TCT | 13.3 | 17.3 | 20.6 | 10 | 14 |
| | AGC | 18.7 | 16.8 | 9.0 | 13 | 9 |
| | AGT | 9.9 | 14.0 | 11.9 | 8 | 8 |
| TER | ACA | 14.3 | 14.9 | 16.4 | 8 | 8 |
| | ACC | 22.6 | 14.0 | 11.9 | 9 | 7 |
| | ACG | 6.6 | 3.2 | 4.0 | 2 | 2 |
| | ACT | 12.6 | 17.4 | 20.4 | 12 | 14 |
| PRO | CCA | 15.4 | 30.6 | 26.2 | 6 | 12 |
| | CCC | 20.6 | 10.5 | 9.0 | 10 | 5 |
| | CCG | 6.8 | 4.6 | 3.2 | 6 | 4 |
| | CCT | 16.1 | 22.2 | 21.7 | 13 | 14 |
| ALA | GCA | 14.4 | 20.5 | 22.3 | 12 | 18 |
| | GCC | 29.7 | 16.6 | 16.2 | 25 | 16 |
| | GCG | 7.2 | 4.7 | 4.4 | 8 | 8 |
| | GCT | 18.9 | 23.2 | 35.2 | 18 | 21 |
| GLY | GGA | 17.4 | 22.7 | 31.4 | 11 | 21 |
| | GGC | 25.3 | 11.9 | 14.0 | 24 | 8 |
| | GGG | 17.5 | 11.0 | 10.0 | 12 | 8 |
| | GGT | 11.5 | 22.1 | 30.0 | 6 | 16 |
| VAL | GTA | 6.1 | 7.5 | 11.5 | 2 | 3 |
| | GTC | 16.2 | 9.0 | 13.8 | 7 | 6 |
| | GTG | 30.7 | 25.8 | 14.4 | 28 | 18 |
| | GTT | 10.2 | 24.4 | 29.4 | 5 | 15 |
| LYS | AAA | 21.9 | 23.2 | 23.2 | 22 | 22 |
| | AAG | 35.2 | 35.2 | 30.7 | 23 | 23 |
| ASN | AAC | 22.3 | 29.2 | 26.0 | 17 | 17 |
| | AAT | 16.5 | 20.2 | 27.8 | 14 | 14 |
| GLN | CAA | 10.8 | 27.4 | 22.5 | 8 | 14 |
| | CAG | 33.8 | 20.7 | 14.1 | 21 | 15 |
| HIS | CAC | 14.7 | 8.9 | 8.9 | 4 | 4 |
| | CAT | 9.3 | 12.1 | 11.1 | 5 | 5 |
| GLU | GAA | 26.4 | 34.6 | 26.7 | 16 | 18 |
| | GAG | 41.6 | 35.8 | 26.2 | 21 | 19 |
| ASP | GAC | 28.9 | 18.8 | 17.2 | 22 | 16 |
| | GAT | 21.5 | 29.7 | 33.0 | 16 | 22 |
| TYR | TAC | 18.0 | 17.1 | 16.6 | 12 | 12 |
| | TAT | 12.3 | 16.2 | 20.6 | 9 | 9 |
| CYS | TGC | 13.8 | 9.9 | 8.1 | 17 | 17 |
| | TGT | 9.9 | 5.5 | 10.1 | 15 | 15 |
| PHE | TTC | 22.1 | 23.5 | 18.1 | 17 | 15 |
| | TTT | 15.8 | 19.3 | 25.2 | 10 | 12 |

TABLE 1-continued

| CODONS | | HUMAN | SOYA | TABACCO | LFU WT | LFU SYN |
|---|---|---|---|---|---|---|
| ILE | ATA | 6.1 | 12.2 | 10.7 | 4 | 4 |
|  | ATC | 24.3 | 15.0 | 13.7 | 7 | 5 |
|  | ATT | 15.0 | 23.7 | 29.4 | 5 | 7 |
| MET | ATG | 22.3 | 20.1 | 22.8 | 4 | 4 |
| TRP | TGG | 13.7 | 11.5 | 13.7 | 10 | 10 |

In carrying out such operation, the value G+C and A+T of the two systems (human and vegetal), the non-tandem repeat of some triplets that may cause shifts in reading, etc. were also taken into due account.

Figure 1:
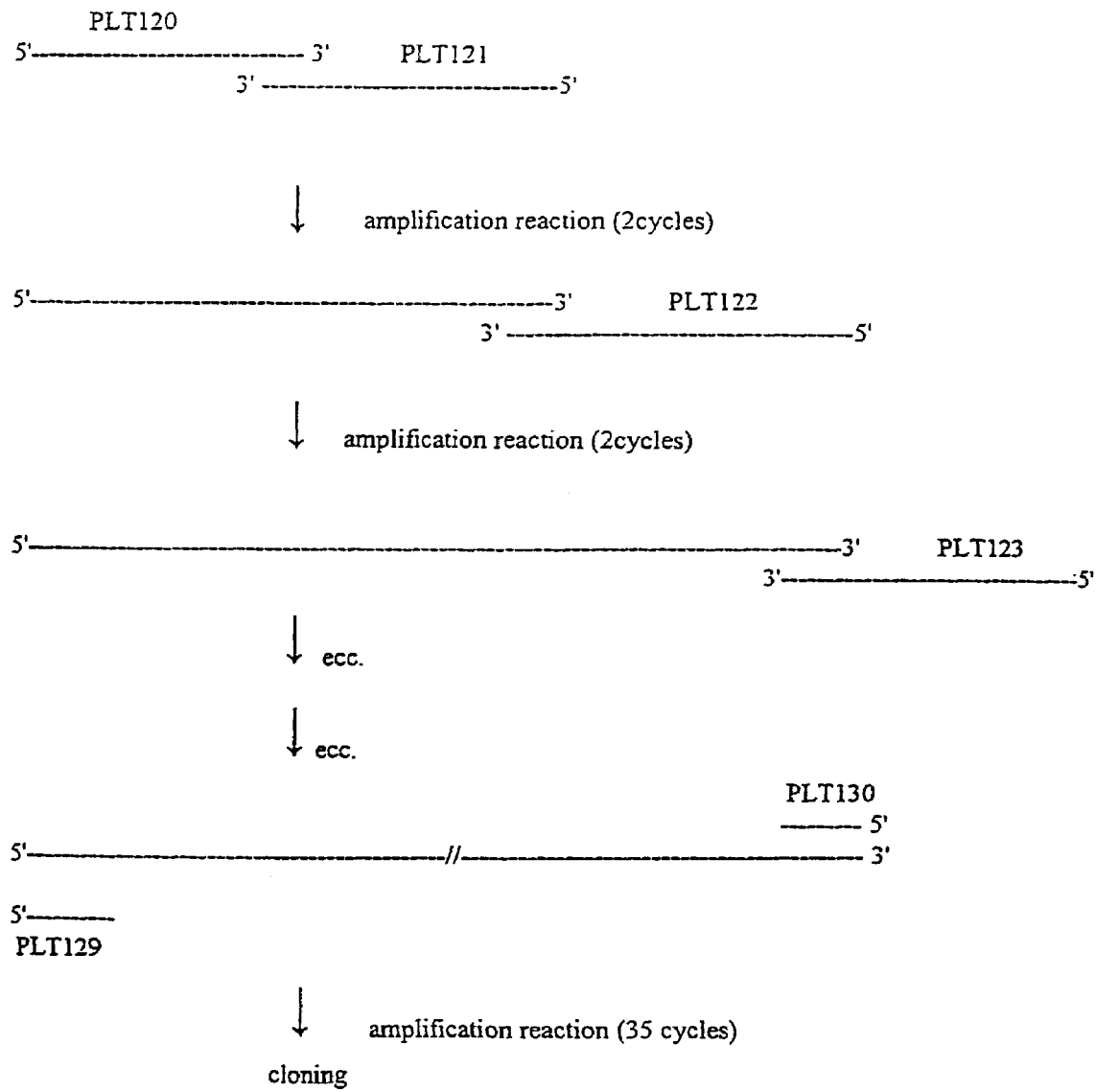
FIG. 1 shows the strategy adopted for the assembly of the synthetic gene encoding human lactoferrin.

Synthetic LFU gene was then obtained using primers reported in the annexed sequence listing from SEQ ID NO:8 to SEQ ID NO:12 and from sequence SEQ ID NO: 15 to SEQ ID NO: 20 and following the assembling strategy reported in FIG. 1, consisting in repeated PCR cycles, using for each cycle different pairs of synthetic primers allowing the gradual elongation and the forming of the final sequence as designed. Similarly on the basis of such final sequence the sequences contained the codons preferably expressed in various species of interest, among which rice, have been obtained.

Figure 7:
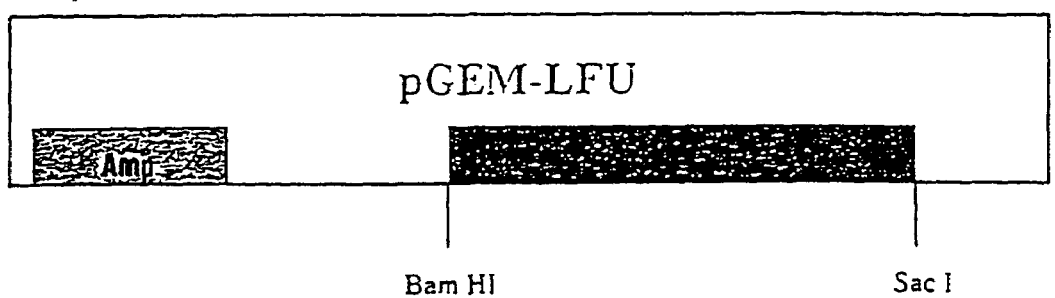
FIG. 7 shows a schematic view of the two plasmids resulting from the cloning of the native gene. LFU into the two vectors pGEM-T and pBI121, carried out in order to obtain plasmids used later on as transformation control.
Figure 7:
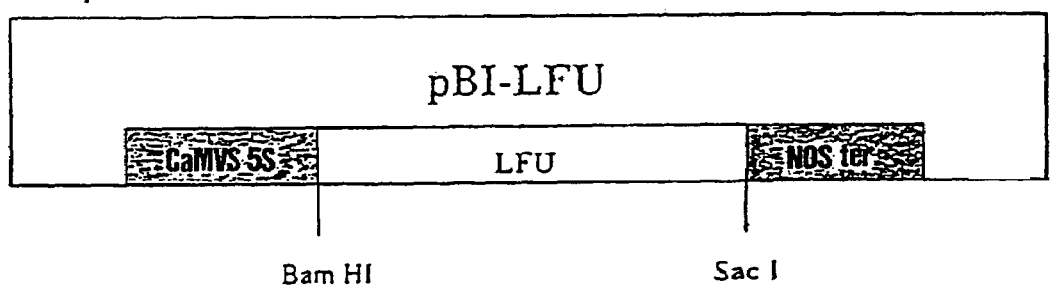

In parallel, also native LFU gene (wild type) encoding human lactoferrin was cloned, always by PCR technique, starting from a cDNA library of human mammalian tissue (Clontech). The gene was recovered in its structural part lacking the signal peptide and the poly-A site and cloned in pGEM-T to form plasmid pGEM-LFU whose map is represented in FIG. 7. Primers designed for amplification are reported in the annexed sequence listing at sequences SEQ ID NO:2 and SEQ ID NO:3; those added the restriction site BamHI at 5' and the restriction site SacI at 3'. After checking the sequence, which tested identical to the published one, the yielded natural gene was cloned in vector pBI121, on sites BamHI and SacI under control of promoter 35S (see FIG. 7), this plasmid (pBI-LFU) was then denominated pBI-35S-LFU and used as control in the genetic transformation experiments and in the subsequent molecular and biochemical analysis.

Concerning the preparation of the recombinant vectors containing the elements that allow the tissue-specific expression of the LFU gene in expression cassettes for plants, we proceeded as follows. In order to obtain the seed-specific expression of the protein the promoters and signal sequences of two genes encoding storage proteins that are very abundant in Soya seeds, i.e. a β-conglycinine (CONG) and a 7S basic globulin (GLOB) were used.

These regulation sequences were isolated and cloned from Soya, Richland variety.

In particular, to clone the two GLOB and CONG sequences PCR technique (PCR=Polimerase Chain Reaction; Innis et al. 1990) was used. In this case genomic DNA extracted from Soya leaves of Richland cultivar was used. Oligonucleotides used for specific amplification are reported in the annexed sequence listing from SEQ ID NO: 4 to SEQ ID NO: 7.

For the GLOB promoter the cloned region includes the entire regulation sequence and the sequence encoding the signal peptide (leader) plus the first codon of the structural sequence, such sequence is indicated with SEQ ID NO: 13 in the annexed sequence listing. For the CONG promoter the cloned region includes the entire regulation sequence and the sequence encoding the signal peptide plus the first codon of the structural sequence, such sequence is indicated with SEQ ID NO: 14 in the annexed sequence listing. For both regulation sequences the most suitable restriction site for insertion proved to be XbaI (TCTAGA), while downstream proved to be BamHI (GGATCC), both absent from the native and synthetic lactoferrin sequence, as highlighted in the following tables 2 and 3.

TABLE 2

```
                 0              1000            2000
                 +---------------+---------------+--
AccI     1   +----≠----------------+---------------+--
AlwI     2   +---------≠-----------+------≠--------+---+-
AlwNI    1   +--------------------+--≠------------+--
AosI     1   +--------------------+≠--------------+--
AvaI     4   +-≠------------------+≠----≠---------+≠--------+--
AvaII    6   +--------≠--≠≠-------+--≠--≠----------+------------≠+-
BalI     2   +----------≠---------+---------------+---------≠-+--
BanI     4   +-----------≠--------+----≠----+-----≠---------+≠--------+--
BanII    2   +-----------≠--------+---------------+---------≠-+--
BbvI     8   +--≠-----≠---≠-------+--------≠≠-≠----+------≠≠--------+--
BncI     5   +------------≠-------2-------≠--------+----≠---+--
BglI     3   +-----------≠--------+----≠----------+---------≠-+--
BglII    2   +--------------------+---≠------+-----≠---------+--
BsmI     1   +--------------------+---------------+----≠------+--
Bsp1286  8   +----------≠-------≠-+--≠-----≠--------+---≠≠≠-------+--
BspMI    1   +--------------------+-----≠---------+--
BstUI    1   +--------------------+---≠-----------+--
BstXI    3   +--------------------+------≠---+-≠-≠---+--
Bsu36I   1   +--------------------+---------------+------+≠
DdeI     8   +-------------≠≠---≠-+---------------+----≠--≠≠-----≠-+≠
DpnI     5   +--------------------+--------≠----+----≠-≠----≠-----+≠----+--
DraII    2   +--------------------+---≠-≠---------+--
DraIII   2   +--------------------+------≠---------+-----------≠-+--
EaeI     3   +------≠---≠---------+---------------+--------≠-------+--
Eco81I   1   +--------------------+---------------+----------+≠
EcoNI    2   +--------------------+---------≠-----+--------≠----+--
EcoO109  2   +----------------≠≠--+---------------+--
EcoRI    1   +--------------------+---------------+--------+≠
```

TABLE 2-continued

| Enzyme | Count |
|---|---|
| EcoRV | 1 |
| Fnu4HI | 10 |
| FokI | 6 |
| FspI | 1 |
| HgiAI | 3 |
| HhaI | 4 |
| HinfI | 6 |
| HinP1I | 4 |
| HpaII | 6 |
| HphI | 3 |
| MaeI | 3 |
| MaeII | 2 |
| MaeIII | 8 |
| MboII | 3 |
| NciI | 5 |
| NcoI | 3 |
| NdeI | 1 |
| NlaIII | 7 |
| PleI | 3 |
| PpuMI | 2 |
| PstI | 2 |
| PvuII | 4 |
| RsaI | 3 |
| Sau3AI | 5 |
| SauI | 1 |
| SfaNI | 4 |
| SmaI | 1 |
| SspI | 2 |
| StuI | 2 |
| StyI | 4 |
| TaqI | 2 |
| XhoII | 3 |
| XmaI | 1 |

TABLE 3

| Enzyme | Count | 0 | 1000 | 2000 |
|---|---|---|---|---|
| AccI | 1 | | | |
| AccIII | 1 | | | |
| AluI | 10 | | | |
| AlwI | 5 | | | |
| AosI | 2 | | | |
| AsuI | 7 | | | |
| AvaII | 6 | | | |
| AvrII | 1 | | | |
| BanI | 2 | | | |
| BanII | 2 | | | |
| BbvI | 3 | | | |
| BcnI | 2 | | | |
| BglI | 2 | | | |
| BglII | 2 | | | |
| BsmI | 2 | | | |
| Bsp1286 | 5 | | | |
| BspMI | 3 | | | |
| BspMII | 1 | | | |
| BstNI | 6 | | | |
| BstUI | 1 | | | |
| BstXI | 3 | | | |
| Bsu36I | 1 | | | |
| Cfr13I | 7 | | | |
| DdeI | 7 | | | |
| DpnI | 8 | | | |
| DraII | 1 | | | |
| DraIII | 2 | | | |
| Eco81I | 1 | | | |
| EcoNI | 1 | | | |
| EcoO109 | 1 | | | |
| EcoRI | 1 | | | |
| EcoRII | 6 | | | |
| EcoRV | 1 | | | |
| Fnu4HI | 4 | | | |
| FokI | 5 | | | |
| FspI | 2 | | | |
| HaeIII | 4 | | | |
| HgiAI | 2 | | | |

TABLE 3-continued

| | | |
|---|---|---|
| HhaI | 3 | +≠-------------------------≠≠----------------------+- |
| HincII | 1 | +-------------------≠--------+-----------------------+- |
| HindIII | 1 | +-----------------------------------≠--------------+- |
| HinfI | 8 | +----≠≠--------≠----------≠---≠≠-+----------≠----≠---+- |
| Hinp1I | 3 | +≠------------------------≠≠----------------------+- |
| HapII | 3 | +-----------------------≠≠---------------≠----+- |
| HphI | 3 | +---≠-----------------≠-----+-----------≠--------------+- |
| MaeI | 5 | +----------------------≠-≠-+-------≠------------+≠ |
| MaeII | 2 | +------------------------+---------≠--≠-------+- |
| MaeIII | 9 | +----≠---------------≠---≠----+-2----≠--------≠≠---≠-------+- |
| MboII | 6 | +---------≠---≠--------≠-≠--+---≠--------≠----------+- |
| MseI | 2 | +-----------------≠-----------+-----------------+- |
| NciI | 2 | +---------------------≠-----------------≠---+- |
| NcoI | 3 | +---------------------------+---------≠----≠-+- |
| NdeI | 1 | +--------------------------------------≠+- |
| NlaIII | 8 | +---------≠-----------≠--------+--------≠-≠≠---≠-+- |
| PleI | 3 | +-----≠------------≠-----+---------------≠---+- |
| PpuMI | 1 | +---------≠-------------+--------------------+- |
| PstI | 2 | +--------------------≠----≠-----------------+- |
| PvuII | 2 | +--------≠--≠-----------+--------------------+- |
| RsaI | 2 | +----------≠---------≠----+--------------------+- |
| Sau3AI | 8 | +--------≠------≠------≠-+-≠----≠-≠--≠---------≠---+- |
| Sau96I | 7 | +--≠-----≠--≠≠-------≠-------+---------------≠----≠+- |
| SauI | 1 | +---------------------+--------------------+≠ |
| ScrFI | 8 | +----≠-----≠--≠---------≠----+-≠----≠----------≠---+- |
| SfaNI | 4 | +-----≠-----------≠------≠≠-+----------------+- |
| SspI | 2 | +-----------------+----------≠-------------≠+- |
| StyI | 5 | +---------------2-+-------≠---------≠-----≠-+- |
| TaqI | 2 | +-------------------≠--+-----------≠--------+- |
| XhoII | 6 | +--------≠-------≠-----≠--+-≠--------≠--------≠---+- |

DNA template was extracted from *Glycine max* leaves, Richland variety, and amplification products match sizes expected for GLOB (1515 pb) and CONG (1163) promoter on the basis of EMBL sequence data.

Figure 2:
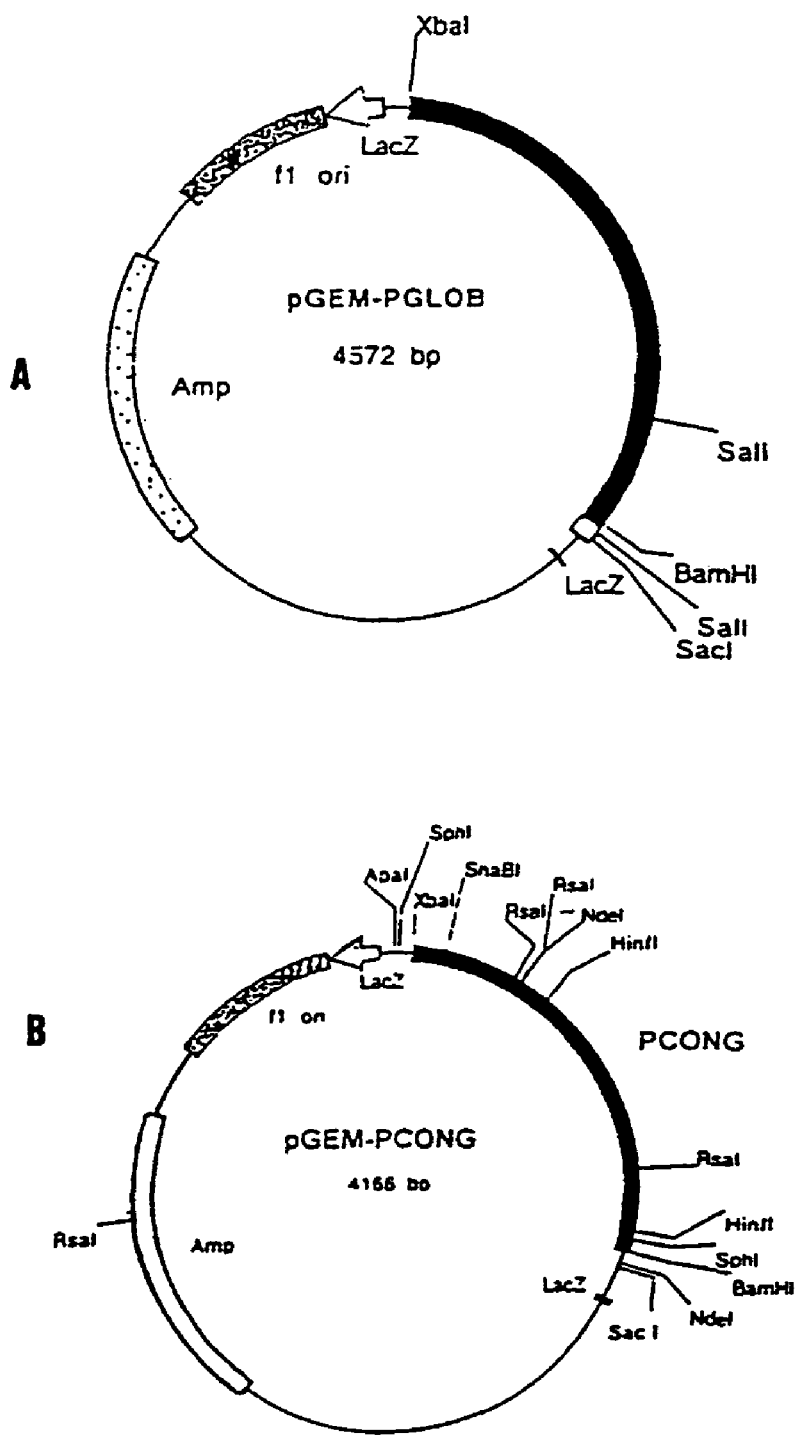
FIG. 2 shows the map of plasmids pGEM-PGLOB(A) and pGEM-PCONG (B) obtained from the cloning of the Soya promoters in plasmid pGEM (Promega), in which the restriction sites used to derive the plasmids are highlighted.
Figure 3:
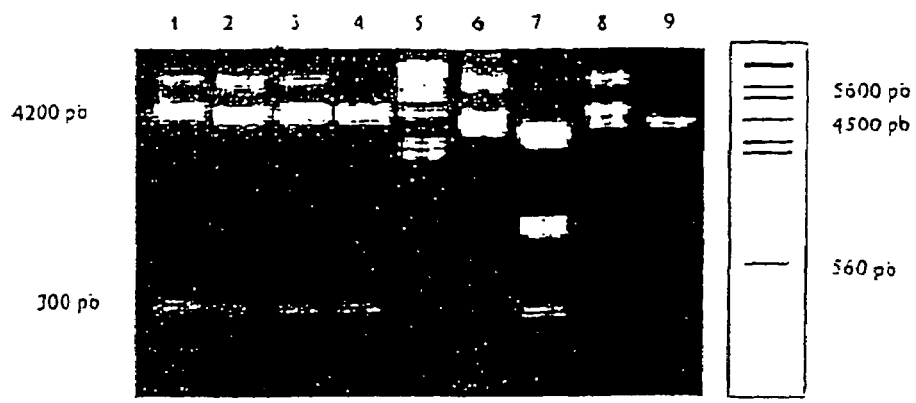
FIG. 3 shows agarose gel electrophoresis analysis of digestion of plasmids pGEM-PGLOB with Sal I (lanes 1, 2, 3 and 4) and pGEM-PCONG CON Sph I (lanes 6, 7, 8 and 9), carried out to test clockwise orientation of the insert. All PGLOB samples tested positive, yielding fragments of the expected sizes. PGLOB 1 is sample 1 selected for the subsequent molecular work. In contrast, PCONG samples did not yield the expected pattern, suggesting the possibility of the presence of errors due to the adopted cloning technique (hypothesis later discarded, see FIG. 6) or due to isolation of a variant of the control region that in the Richland variety differs from the one of the disclosed sequence (Dare variety). Sample 5 is lambda marker HindIII.
Figure 4:
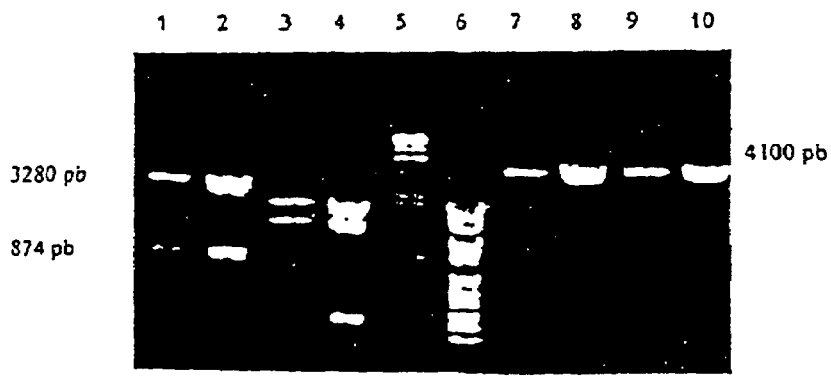
FIG. 4 shows agarose gel electrophoretic analysis of the restriction pattern of two plasmid pGEM-PCONG clones with enzymes Nde I (lanes 1 and 2), Rsa I (lanes 3 and 4), and SnaB I (lanes 9 and 10), carried out in order to test orientation and identity of the constructs. Cuts with Nde I, Apa I and SnaB I yielded the expected patterns in contrast to the cut performed with Rsa I; this results are justified from the differences found in sequence and reported in FIG. 6. In lanes 5 and 6 markers of molecular weight λ-DNA Hind III and Marker IV (Boehringer) respectively are present.
Figure 5:
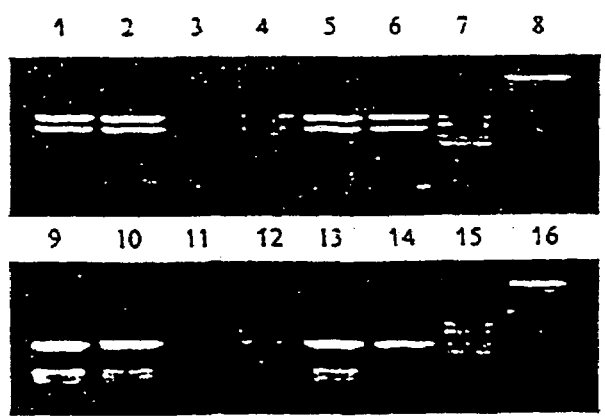
FIG. 5 shows electrophoretic analysis of the restriction of various clones of plasmid pGEM-PCONG with Rsa I (lanes 1-6) and Hinf I (lanes 9-14) enzymes in order to test identity of constructs. In both cases the obtained pattern do not mirror the expected ones, but are conserved among the different clones, thereby suggesting their being due to differences in the original sequence with respect to the published restriction map and not to errors in the amplification phase with Taq polymerase or in the cloning. Adopted markers are λ-DNA Hind III and Marker IV.
Figure 6:
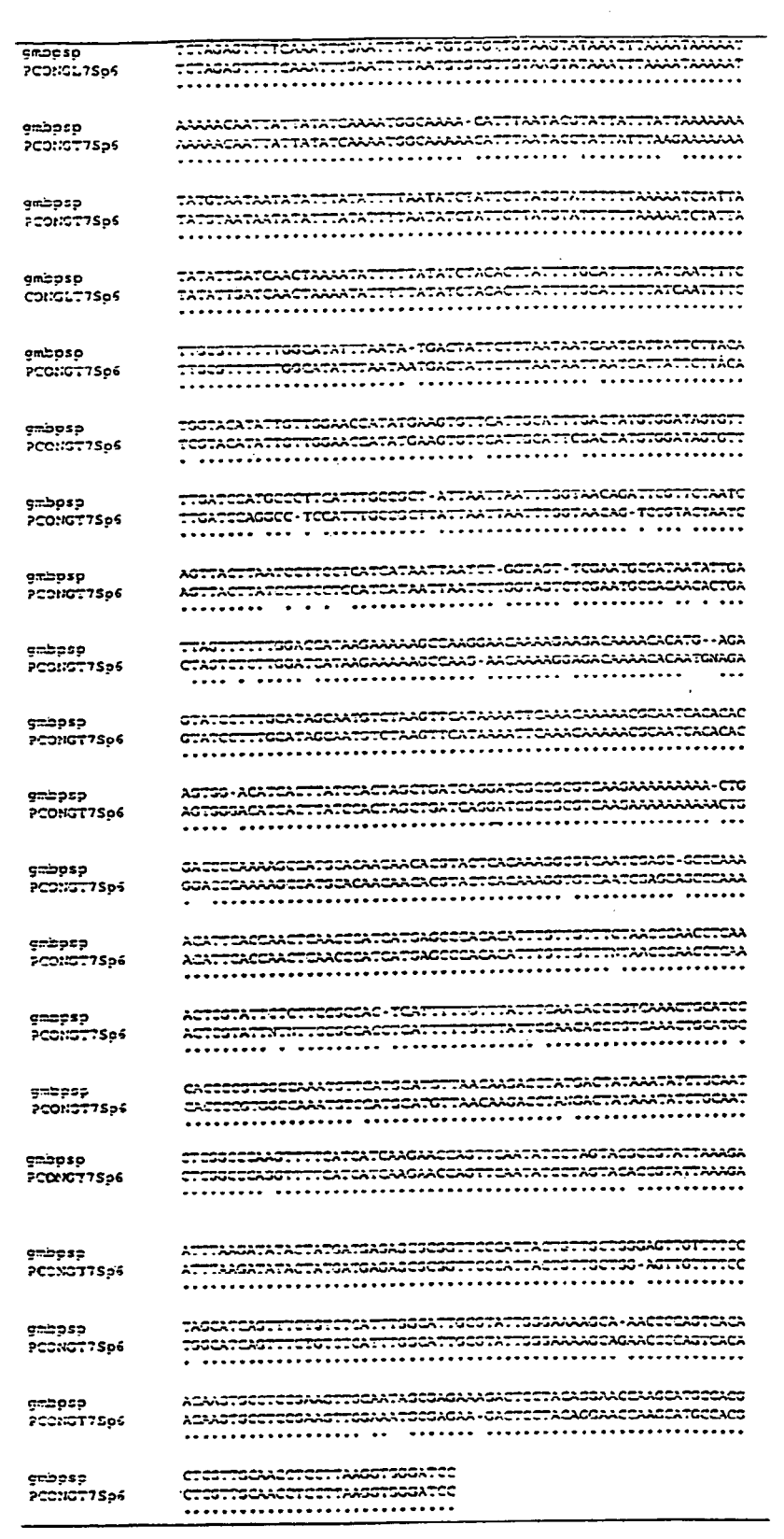

Therefore, starting from fragments amplified by ligation in vector pGEM-T, the two vectors pGEM-PGLOB and pGEM-PCONG, whose map is reported in FIG. 2, were constructed. Yielded plasmids were tested by restriction analysis performed with several enzymes chosen among those cleaving in a limited number and with an overall sequence distribution (see FIGS. 3, 4 and 5) and a clone for each type was selected and sequenced. Sequenced clones showed to be significantly different from the expected sequence. As an example, a comparison between the data bank promoter CONG sequence and the one obtained sequencing clone pGEM-pCONG is reported in FIG. 6. A 5% difference was detected, therefore the two promoters can be considered as different.

Figure 8:
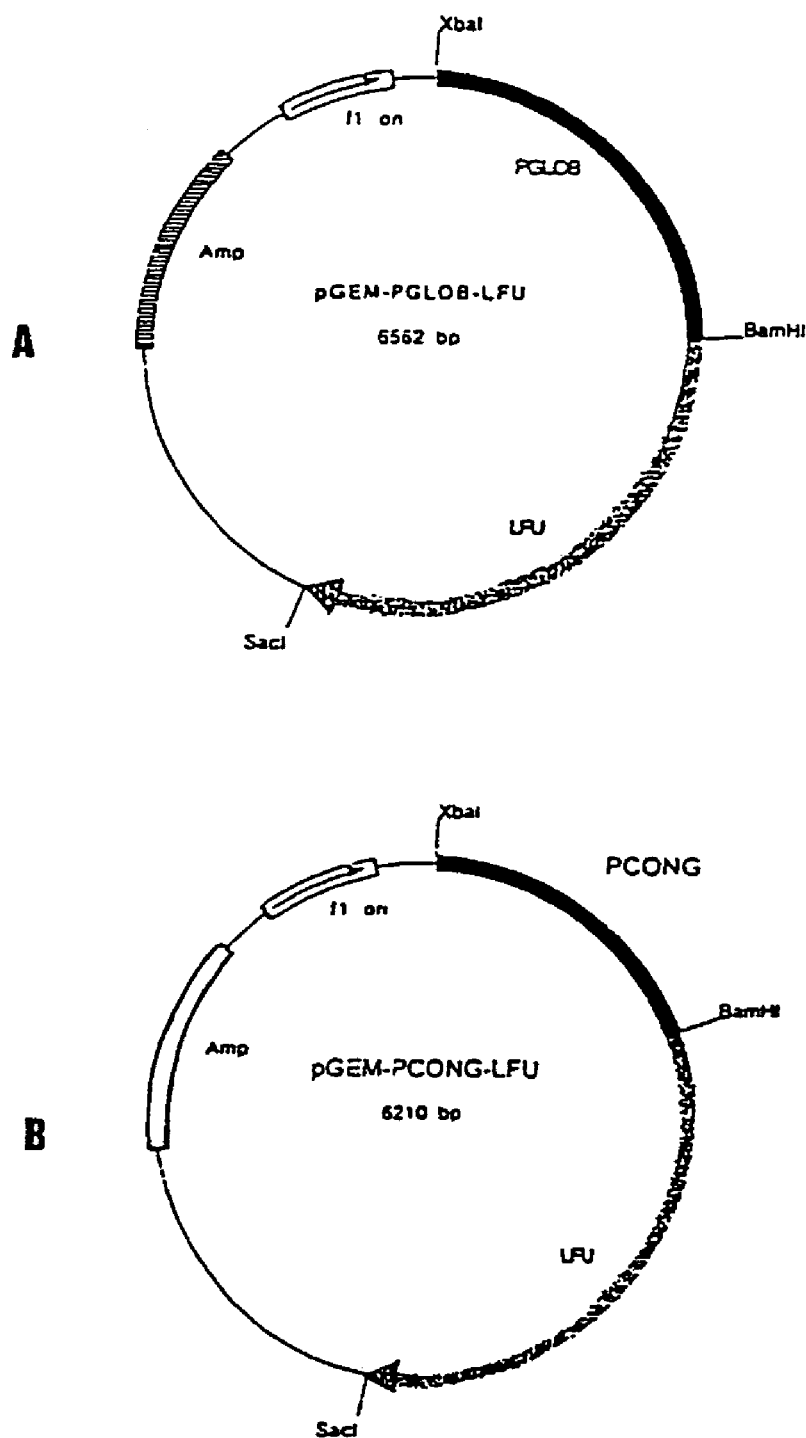
FIG. 8 shows the map of the two plasmids resulting from synthetic LFU gene cloning into vectors pGEM-PGLOB and PGEM-PCONG, i.e. plasmids pGEM-PGLOB-LFU (A) and pGEM-PCONG-LFU (B), respectively.

The synthetic gene for human lactoferrin was cloned at first in plasmids pGEM-PGLOB and pGEM-PCONG, cut with enzymes BamHI-SacI, to form plasmids PGEM-PGLOB-LFU and pGEM-PCONG-LFU respectively, whose map is disclosed in FIG. 8, and then the construct XbaI-SacI transferred in vector pBI101 cut with the same enzymes. In the event of a plant transformation carried out with physical means, as for rice in our case, plasmids pGEM-PGLOB-LFU and pGEM-PCONG-LFU, can be directly used after addition of a terminator, in cotransformation with a vector containing the selection marker (e.g., a PUC-type vector containing the gene for hygromycin resistance). Resulting plasmids pBI-PGLOB-LFU and pBI-PCONG-LFU, whose map is reported in FIG. 9, were used in the genetic transformation of the plants after an accurate control carried out by restriction with various enzymes to assay the correct integration of the DNA construct (FIGS. 10 and 11). Plasmids pBI-35S-LFU, pBI-PGLOB-LFU and pBI-PCONG-LFU were transferred in *A. tumefaciens* EHA105 strain cells, made competent by electrophoresis. Strains containing the three plasmids were used to transform about 450 leaf disks (LD) of tobacco, Petit Avana variety. Formation first of shoots and then of roots was induced from calluses formed on leaf disks (LD) in presence of kanamycin. Once rooted, plants were potted and at least 50 kanamycin-resistant plants were analyzed for each construct. The same plasmids containing, this time, the hygromicyn-resistance genes marker, are used also for the transformation of rice. In this case in particular 40 plants hygromicyn resistant were analyzed.

Plants $T_0$, of rice as well as of tobacco, were tested by PCR technique (FIG. 12), assaying the presence of the lactoferrin gene inside the genome of the tested plants; plants $T_1$ were assayed by Southern analysis (FIG. 13), that compared to PCR technique allows a more accurate testing of the transgene presence in the genome, and with Western analysis (FIG. 14) allowing detection of genic product and therefore the functionality of inserted gene.

All plants with native LFU gene under control of promoter 35S led to accumulation of a protein, recognized by LFU-specific antibodies, of a molecular weight lower than 50 KDa. This protein was found in small amounts in young leaves, becoming undetectable in the fully developed leaves. Plants of rice as well as of tobacco transformed with the two constructs pBI-PGLOB-LFU and pBI-PCONG-LFU produce and accumulate exclusively in seed a protein having a molecular weight of 82 KDa corresponding to the glycosilated human protein as shown by electrophoretic analysis of extracted proteins and by the related Western Blotting carried out with LFU-specific antibodies (see FIG. 15). Presence of recombinant protein exclusively in the seed and not in the leaves was assayed in all the examined transgenic plants (about 50 for the two constructs) with Western techniques.

Recombinant LFU protein isolated from seed and purified with HPLC technique showed to be identical to the native protein concerning its iron binding capacity and its inhibiting effect towards the examined bacterial strains. Treatment with a deglycosilating enzyme confirms the presence of posttranslational modifications in all alike, at present at least in quantitative terms, to those present in native lactoferrin as highlighted by Western analysis, the results of which are disclosed in FIG. 16.

Moreover, the contribution of iron consequence of the introduction of the lactoferrin gene in rice plants was assessed. In particular, in the following table 4 results in terms of iron content of some transgenic lines of the Ariete and Rosa Marchetti varieties transformed with plasmids pBI-PCONG-LFU and pBI-PGLOB-LFU are reported. Iron content was measured by atomic absorption after flour mineralization with $HNO_3$ e $H_2O_2$.

Table 4: Analysis of iron content in Ariete (A) and Rosa Marchetti (RM) varieties and of the respective transgenic lines capable of in-seed accumulation of protein lactoferrin.

| Sample | Fe Concentration (µg/g) | RSD |
|---|---|---|
| Ariete | 34.3 | 3.0 |
| A cl. 2-3 | 48.5 | 0.7 |
| A cl. 5-1 | 86.5 | 1.8 |
| A cl. 6-2 | 117.0 | 1.2 |
| A cl. 6-3 | 72.4 | 3.2 |
| Rosa Marchetti | 23.5 | 3.6 |
| RM cl. 5-3 | 64.5 | 2.8 |
| RM cl. 2-5 | 76.5 | 2.4 |
| RM cl. 3-6 | 52.7 | 3.0 |
| RM cl. 4-1 | 48.2 | 1.7 |

It is therefore evident from all of the above-reported results that using the native gene, described in the literature, for human lactoferrin under control of the traditional promoters used for genetic transformation of plants, human protein lactoferrin cannot be produced in relevant amounts, in a stable form and with the posttranslational modifications typical of this protein.

So far a general description has been given of the present invention. With the aid of the following examples, a more detailed description will now be given of specific embodiments thereof, with the purpose of giving a clearer understanding of objects, features, advantages and methods of application of the invention.

EXAMPLE 1

*Agrobacterium Tumefaciens*-Mediated Tobacco Transformation

Day 1

A small amount of *Agrobacterium tumefaciens* of strain EHA 105, taken from a petri plate culture with a sterile loop so as not to exceed in the amount thereby avoiding subsequent problems in controlling bacterial proliferation on plated leaf disks, was inoculated in 2 ml of sterile LB. Then, from a healthy tobacco plant of Petit Avana variety a leaf showing no alteration whatsoever, conversely showing optimal turgor conditions, was taken. The leaf was briefly washed in bidistilled water to remove surface impurities, immersed for 8 min in a 20% sodium hypochlorite and 0.1% SDS solution and left to dry under a vertical flow hood. From then on all steps were carried out under hood. In particular, the leaf was immersed in 95% ethanol and shaken in order to completely wet the pages thereof (letting the petiole emerge) for 30-40 sec. The leaf was then allowed to dry out completely.

Disks were obtained from the entire leaf surface with an ethanol-sterilized punch, let fall on plates with MS10 free of antibiotics; in particular, the ratio of 30 disks per plate was not exceeded.

Next, 2 ml LB+(just inoculated) *Agrobacterium* were poured on plate, and the bacterial suspension was evenly spread over the entire plate with a gentle rotatory movement, in order to obtain an homogeneous bacterial distribution among the disks. LB in excess was carefully aspirated with a pipette. In the course of those steps at all times a parallel negative control was provided by means of a plate to which nothing, or only LB was added.

Then plates were incubated at 28° C. for 24-48 hours in constant lighting conditions, and bacterial growth was indicated by the appearance of a thin opaque layer spreading over the entire plate.

Day 2

Leaf disks (=LD) were carefully transferred on a plate with MS10+500 mg/l cefotaxime, and incubated at 28° C. for 6 days in constant lighting conditions. This step determines the *Agrobacterium* inactivation.

Day 8

LD were then carefully transferred on a plate with MS10+500 mg/l cefotaxime and 200 mg/l Kanamycin, and incubated at 28° C. for 14 days in constant lighting conditions. This step determined a selection of the transformed plants: in fact, gene of kanamycin resistance was carried by the plasmid inserted in *Agrobacterium*.

Day 22

LD, that in the meantime had grown developing a callus, were carefully transferred on a plate with MS10+500 mg/l cefotaxime, 200 mg/l Kanamycin and 500 mg/l carbenicillin, and incubated for 6 days. This step determines elimination of the *agrobacteria* possibly survived to the previous antibiotic treatments (a very frequent occurrence).

Day 28

LD were transferred again on MS10+500 mg/l cefotaxime and 200 mg/l Kanamycin, and incubated until shooting. When shoots showed at least two leaves, they were separated from the callous mass and transferred on the radication medium: MS0+500 mg/l cefotaxime and 200 mg/l Kanamycin.

At the appearance of roots, seedlings were extracted from the plate, freed from agar residues, gently washed in running water and planted out in loam and sand (2:1) inside small plastic pots. Soil was previously saturated with water, then pots were covered with transparent plastic lids to preserve high humidity conditions, and placed in a growth chamber at room temperature, with a daily 16-hour lighting period.

EXAMPLE 2

Rice Transformation by Physical Methods

Rice seeds of Ariete and Rosa Marchetti varieties were harvested at milky ripening, when the endosperm is still liquid. The embryo was isolated with a lancet after removal of the two glumes. Immature embryos are of different size and shape, depending on the number of days elapsed from blooming: The ones deemed most suitable for the in vitro culture and the successive transformation, i.e. those of an 1.5 mm average size, were cultured on a medium containing 2,4-D auxine to promote scutellum cell division and suppress differentiation of young embryos, obtaining cellular proliferation of the scutellum area. At this stage embryos underwent bioholistic transformation, with the following parameters: particle size 1.5-3 µm, particle concentration 500 µg, membrane rupturing pressure 1.100 psi, membrane-microcarrier gap 6 mm, microcarrier stop-point gap 6 mm, stop-point target gap 10.5 cm.

Transformation was effected by a cotransformation technique, using as a selectable marker the gene for hygromycin on plasmid pROB5. Cotransformation was effected with a total DNA concentration of 1 µg/µl using 0.6 µg DNA for bombing and with a selectable plasmid/suitable plasmid (pROB5 with pBI-PGLOB-LTU or with pBI-CONG-LTU) ratio of 1:1 assessed on the number of molecules (abt. 1:4 in amount).

Osmotic conditions of the plant material were optimized carrying out a preculture on 3% saccharose and plasmolysis prior to bombing on MS with 10% saccharose for 1 hour. 24 hours after bombing with PDS-1000/He bioholistic system the material was transferred on 3% saccharose medium.

For selecting the transformational events, bombed tissue underwent selection in presence of hygromycin B (Duchefa). 1 day after bombing embryos were transferred on solid MS medium, additioned with 2 mg/l 2,4-D auxine, 50 mg/l cefotaxime, 50 mg/l hygromycin B, 3% saccharose and 0.35% agarose. One week later embryos were transferred on R2 liquid medium (Ohira et al., 1973) containing 1 mg/l thiamine, 50 mg/l cefotaxime, 50 mg/l hygromycin B and 3% saccharose, pH 5.8, in 190 ml plastic vessels (Greiner). Liquid cultures were shaken at 90 rpm and 28° C. in the dark, replacing the liquid medium every 7 days. After 3-4 weeks resistant calluses formed on the embryo surfaces are transferred on R2 solid medium additioned with MS vitamins, 2 mg/l 2,4-D auxine, 50 mg/l cefotaxime, 50 mg/l hygromycin B, 60 g/l saccharose and 0.5% agarose and maintained for 2-4 weeks, until formation of embryogenic structures.

At the formation of embryogenic structures calluses were transferred on solid MS regeneration medium containing 2 mg/l BAP, 0.2 mg/l NAA, 3% maltose, 50 mg/l hygromycin B, 50 mg/l cefotaxime and 0.8% agarose.

Embryogenic calluses were maintained in phytotron at 28° C. with 16 hours of lighting to induce formation of shoots, that, once formed, were transferred on hormone-free ½ MS radication medium, 3% saccharose and 0.3% gelrite. After 3-4 weeks at 28° C., seedlings were transferred in a Yoshida solution (Yoshida et al. 1976) and maintained at 25/19° C. day/night with a 11 h day length. After 4 weeks plants were potted and grown in hothouse until the cycle end.

EXAMPLE 3

Purification of Lactoferrin Protein from Different Tissues of the Plant and Assessment of Molecular Weight.

Extraction of all the proteins of tobacco seed was performed grinding the seeds in liquid nitrogen in presence of an extraction buffer (0.5 M saccharose, 0.1% ascorbic acid, 0.1% Cys-HCl, 0.01 M Tris-HCl, 0.05M EDTA pH 8).

Then the solution was centrifuged for 30 minutes at 14.000 rpm at 4° C. and the supernatant was kept with the soluble proteins.

Then the solution was filtered with filters of 0.2 µm porosity, and the lactoferrin partially purified by removing proteins of a molecular weight lower than 30 KDa by centrifugation in Centricon 30 column (Amicon).

The lactoferrin was further purified by HPLC chromatography on Resource Q column (Pharmacia) at a weak cationic exchange, with elution in phosphate buffer pH 7 and NaCl gradient 20-100%. The peak corresponding to lactoferrin eluted at 0.7 M NaCl.

The fractions of the elution range were reunited and filtered in Centricon 30 to remove salt.

For the lactoferrin extraction from tobacco leaves, up to the centrifugation step we proceeded as in the case of extraction from seed, then the supernatant was additioned with 60% $(NH_4)_2SO_4$ and left shaking in ice for 60 min.

Then the solution was centrifuged at 14.000 rpm for 15 minutes at 4° C., the pellet recovered and then suspended again in phosphate buffer pH 6.8.

For the assessment of molecular weight in SDS-PAGE, the colorant (SDS loading buffer) was additioned to the lactoferrin sample (20 µl) and the samples were loaded onto 8% polyacrilamide minigels. Running conditions were: initially 10 mA, and 20 mA for the entire run, in Tris-glycine 1× buffer. Then the gel was stained by Silver staining technique and the molecular weight assessed referring to molecular weight standards.

EXAMPLE 4

Western Analysis of the Lactoferrin Protein Produced in Plant and Deglycosilation Thereof.

Lactoferrin purified from seed according to example 2, after electrophoretic separation on acrylamide gel was transferred by electroblotting (buffer 25 mM Tris, 192 mM glycine, 20% methanol, 45 V at 4° C.) to a nitrocellulose membrane (BA85 Schleicher and Schull).

The membrane with the immobilized protein was shaken for 60 min in TBS-T 5% Skin milk solution and then, after some washings, with the same solution containing the primary antibody in a 1:2500 ratio.

After reaction with primary antibody the membrane washed and placed in contact with the secondary antibody (Anti-Rabbit peroxidase conjugate), always in TBS-T Skin milk solution, in a 1:12.000 ratio.

After reaction with secondary antibody the membrane washed several times and placed in contact with Amersham's chemiluminescence kit ECL.

The membrane was then exposed in contact with a photoplate (Hyperfilm MP, Amersham) in darkroom for variable lengths of time.

Deglycosilation with N-glycosidase F enzyme (Boehringer Man.) was carried out using 10 µl in volume of glycopeptide (10 µg) denatured in 0.1% SDS brought to boiling point for 2 min.

To this solution 90 µl of buffer (20 mM phosphate buffer pH 7.2, 50 mM EDTA pH 8, 10 mM sodium azide, 0.5& NP40, 1% β-mercaptoethanol) were additioned and it was brought to boiling point again for 2 min, then cooled at 37° C.

To the resulting 100 µl 1 U of N glycosidase F was additioned and let incubate at 37° C. for 18 hours. Then the reaction product was analyzed on SDS-PAGE gel and the lactoferrin protein detected by Western technique.

Glossary

The term "recombinant polynucleotide", as it is used here to characterize a polynucleotide useful in the production of lactoferrin, relates to a polynucleotide of genomic origin, cDNA, semi-synthetic or synthetic, that, by virtue of its origin or manipulation: 1) is not associated to a portion or to the totality of the polynucleotide to which it is associated in nature, and/or 2) is linked to a polynucleotide differing from that to which it is associated in nature, or that 3) does not exist in nature.

The term "polynucleotide", as it is used here, relates to a polymeric form of nucleotides of any length, ribonucleotides as well as deoxyribonucleotides. This term exclusively refers to the molecule primary structure. Hence, the term includes single and double stranded DNA as well as single and double stranded RNA. It also includes modified forms of the polynucleotide, e.g. by methylation, phosphorilation or "capping", and non modified forms.

An <<expression cassette for plants>> relates to a recombinant polynucleotidic sequence obtained by linking together operatively various elements constituted by the polynucleotidic sequences that determine the in plant expression of a character and that are easily transferable as discrete constructs, from a vector to another by enzymatic restriction.

A "vector" is a replicon to which another polynucleotidic fragment is added, in order to effect the replication and/or expression of the fragment itself.

A "replicon" is any genetic element, for instance a plasmid, a chromosome, a virus, that behaves as an autonomous polynucleotidic replication unit inside a cell; therefore it can replicate autonomously.

"regulation sequence" refers to polynucleotidic sequences that are needed to effect the expression and/or the secretion of coding sequences to which they are bound. The nature of these regulation sequences differs depending on the host; in prokaryotes those regulation sequences usually include promoter, binding site of ribosomes and terminators; in eukaryotes these regulation sequences usually include promoters, terminators and, in some cases, enhancers. In addition, in prokaryotes as well as in eukaryotes, leader sequences control the host cell secretion of the expressed polypeptide. The term "regulation sequences" includes, at least, all components whose presence is required for expression, and may also include additional components whose presence is advantageous, for instance leader sequences.

A <<leader>> sequence is a polynucleotidic fragment, usually short, encoding a transport signal of the protein fused thereto and leading the protein transfer into specific cellular compartments. If the transfer takes place through the endoplasmic reticulum the protein undergoes specific post-transcriptional modifications.

"Operatively linked" relates to a juxtaposition wherein the above described components are in a relation enabling them to function in the expected way. A regulation sequence <<operatively linked>> to a coding sequence is linked in such a way that the coding sequence expression takes place in conditions that are compatible with the regulation sequences.

AN open reading frame, ORF is a polynucleotidic sequence region encoding a polypeptide; this region can represent a portion of coding sequence or a complete coding sequence.

A "coding sequence" is a polynucleotidic sequence that is transcribed in the mRNA and/or translated in the polypeptide when placed under control of appropriate regulation sequences. The ends of the coding sequence are determined by a translation start codon at 5' and by a translation stop codon at 3'. A coding sequence can include, without being limited to, mRNA, cDNA, and recombinant polynucleotidic sequences.

"Recombinant host cells", "host cells", "cells", "cell lines", "cell cultures" and other terms indicating microorganisms or cell lines of superior eukaryotes, cultivated as unicellular entities, are used here in an interchangeable way. They relate to cells that can be, or have been, used as hosts for recombinant vectors or other transfer polynucleotides, including the progeny of the cell that was originally transformed. It is implicit that, due to random or deliberate mutations, the progeny of a single parental cell need not necessarily be identical to the parental cell from a morphological and a genetic point of view. Progenies of the parental cell that are sufficiently similar to the ancestor cell and can be characterized for their salient capacity, as e.g., the presence of a nucleotidic sequence encoding the peptide of interest, are included in the progeny understood according to this definition and fall within the same terms.

For <<cell aggregation>> a group of cells that are not structured in an organized tissue, but result from an undifferentiated proliferation of cells maintained in particular conditions of hormonal concentration.

"Transformation", as it is used here, refers to the insertion of a exogenous polynucleotide in a host cell, regardless of the method used for the insertion itself, e.g. direct acquisition, *Agrobacterium* infection, sexual reproduction. The exogenous polynucleotide can be maintained as a non integrated vector, for example a plasmid or, alternatively, it can integrate in the host genome.

As it is used here, the term "polypeptide" relates to the amino acidic product of a sequence encoded inside a genome and does not relate to the specific length of the product: accordingly, peptides, oligopeptides and proteins are included in the definition <<polypeptide>> This term does not relate to the post-expressional modifications of the peptide, as e.g. glycosilation, acetylation, phosphorilation, sialilation and the like.

A "wild type polypeptide", has an amino acidic sequence identical to the one encoded in the genome of the organism source of the coding sequence.

"Native lactoferrin" and analogous terms relate to the lactoferrin isolated from the source in which it is usually produced in nature by a genome existing in nature.

A "non-native polypeptide" refers to a polypeptide that is produced in a host differing from the one wherein it is produced in nature.

REFERENCES

Anderson B. F., Baker H. M., Norris G. E., Rice D. W., Baker E. N. 1989. J. Mol. Biol. 209:711-734.

Baeuerle P. A. 1995. Nature 373:661-662.

Bezault J. A., Bhimani R., Wiprovnick J., Furmanski P. 1994. Cancer Res. Baltimore 54:2310-2312.

Boesman Finkelstein M., Sciortino C. V., Finkelstein R. A., Spik G., Montreuil J., Chrichton R. R., Mazurier J. 1985. Proc. 7th Int. Conf. Prot. Iron Metab. 251-260.

Bray E., Naito S., Pan N., Anderson E. Dubé P. H., Beachy R. N. 1987. Planta 172:364-370.

Bustos M. M., Begum D., Kalkan F. A. Battraw M. J., Hall T. C. 1991. EMBO J. 10:1469-1479.

Chamberland S., Daigle N., Bernier F. 1992. Plant Mol. Biol. 19:937-949.

Fontes E. P. B., Silva C. J., Carolino S. M. B., Figueiredo J. E. F., Batista D. P. O. 1996. Braz. J. Genetics 19:305-312.

Fraley R., Schell J. (eds.) 1991. Curr. Opinion Biotechnol, 2:145-210.

Fujiwara T., Beachy R. N. 1994. Plant Mol. Biol. 24:261-272.

Galili G., Altschuler Y., Levanony H. 1993. Trends in Cell Biol. 3:437-442.

Gelvin S. B., Schilperoort R. A. 1995. Plant Molecular Biology Manual. Kluwer Acad. Pub., London.

Glick B. R., Pasternak J. J. 1994. Molecular Biotechnology. ASM Press, Washington, p. 113.

Grover M., Giouzeppos O., Schnagl R. D., May J. T. 1997. Acta Paediatr. 86:315-316.

Hambraeus L., Lonnerdal B. 1993. Indigenous Antimicrobial Agents in Milk-Recent Developments. Pp. 97-107.

Harada J. J., Barker S. J., Goldberg R. B. The Plant Cell, 1:415-425.

He J., Fumanski P. 1995. Nature 373:721-724.

Hirano H., Kagawa H., Okubo K. 1989. 31:731-735.

Ilgoutz S.C., Knittel N., Min Lin J., Sterle S., Gayler K. R. 1997. Plant Mol. Biol. 34:613-627.

Innis M. A., Gelfand D. H., Sninsky J. J., White T. J. 1990. PCR Protocols: a guide to methods and applications. Academic Press, New York.

Kagawa H., Yamauchi F., Hirano H. 1987. FEBS Lett. 226:146-149.

Katagiri F., Lam E., Chua N. H. 1989. Nature 340:727-730.

Kermode A. R. 1996. Critical Rev. In Plant Sciences, 15:285-423.

Komatsu S., Hirano H. 1991. FEBS Lett. 294:210-212.

Lessard P. A., Allen R. D., Bernier F., Crispino J. D., Fujiwara T., Beachy R. N. 1991. Plant Mol. Biol. 16:397-413.

Lonnerdal B., Iyer S. 1995. Ann. Rev. Nutr. 15:93-110.

Mann D. M., Romm E., Migliorini M. 1995. J. Biol. Chem. 269:23661-23667.

Marchetti M., Longhi C., Conte M. P., Pisani S., Valenti P., Seganti L. 1996. Antiviral Res. 29:221-231.

Miehlke S., Reddy R., Qsato M. S., Ward P. P., Conneely O. M., Graham D. Y. 1996. J. Clin. Microbiol. 34:2593-2594.

Mitra A., Zhang Z. 1994. Plant Physiol. 106:977-981.

Naito S., Dubé P. H., Beachy R. N. 1988. Plant Mol. Biol. 11:109-123.

Nakajima M., Shinoda I., Samejima Y., Miyauchi H., Fukuwatari Y., Hayasawa H. 1997. J. Cell Physiol. 170:101-105.

Nishizawa N. K., Mori S., Watanabe Y., Hirano H. 1994. Plant Cell Physiol. 35:1079-1085.

Nuijens J. H., van Berkel P. H., Geerts M. E., Hartevelt P. P., de Boer H. A., van Veen H. A. 1997. J. Biol. Chem. 272:8802-8807.

Oguchi S., Waker W. A., Sanderson I. R. 1995. Biol. Of the Neonate, 67:330-339.

Ohira K., Ojima K., Fujiwara A. 1973. Studies on the nutrition of rice cell culture. 1. A simple defined medium for rapid growth in suspension culture. Plant Cell Physiol. 14:1113-1121.

Okita T. W. 1996. Ann. Rev. Plant Physiol. Plant Mol. Biol. 47:327-350.

Owen M. R. L., Pen J. 1996. Transgenic plants: A production system for industrial and pharmaceutical proteins. J. Wiley e Sons, New York.

Paule-Eugene N., Dugas B., Kolb J. P., Damais C., Braquet P., Paubert-Braquet M., Rialland J. P. 1993. Comp. Rendus Acad. Sci., Series 3, Sci. De la Vie, 316:113-119.

Penco S., Pastorino S., Bianchi-Scarra G., Garre C. 1995. J. Biol. Chem. 270:12263-12268.

Perez-Grau L., Goldberg R. B. 1989. The Plant Cell, 1:1095-1109.

Petschow B. W., Talbott R. D. 1991. Pediatric Res. 29:208-213.

Riggs C. D., Voelker T. A., Chrispeels M. J. 1989. Plant Cell, 1:609-621.

Salmon V., Legrand D., Georges B., Slomianny M. C., Coddeville B., Spik G. 1997. Protein Expr. Purif. 9:203-210.

Samaranayake Y. H. et al. 1997. APIMIS, 105:875-883.

Shewry P. R., Napier J. A., Tatham A. S. 1995. The Plant Cell, 7:945-956.

Soukka T., Lumikari M., Tenovuo J. 1991. Microbial Ecol. In Health and Dis. 4:259-264.

Steiner T. S. et al. 1997. Clin. Diagn. Lab. Imm. 4:719-722.

Stowell K. M., Rado T. A., Funk W. D., Tweedie J. W. 1991. Biochem. J. 276:349-355.

Superti F., Ammendolia M. G., Valenti P., Seganti L. 1997. Med. Microb. Imm. 186:83-91.

Swart P. J., Kuipers M. E., Smit C., Pawels R., De Bethune M. P., De Clercq E., Meijer D. K. F., Huisman J. G. 1996. AIDS Res, and Human Retroviruses, 12:769-775.

Teraguchi S., Ozawa K., Yasuda S., Shin K., Fukuwatari Y., Shimamura S. 1994. Biosc. Biotech. And Biochem. 58:482-487.

Teraguchi S., Shin K., Ozawa K., Nakamura S., Fukuwatari Y., Tsuyuki S., Namihara H., Shimamura S. 1995. Appl. Env. Microb. 61:501-506.

Tomita M. 1993. Ind. Antimicr. Agents of Milk-Recent Develop. pp. 7-12.

Van Berkel P. H. C., Geerts M. E. J., van Veen H. A., Mericskay M., De Boer H. A., Nuijens J. H. 1997. Biochem. J. 328:145-151.

Yoshida S., Forno D. A., Cook J. H., Gomez K. A. (eds.) 1976. Routine procedures for growing rice plants in culture solution. In: Laboratory manual for physiological studies of rice. IRRI. Los Banos pp. 61-66

Ward P., Lo J. Y., Duke M., May G. S., Headon D. R., Conneely O. M. 1992. BioTechn. 10:784-789.

Ward P., Piddington C. S., Cunningham G. A., Zhou X., Wyatt R. D., Conneely O. M. 1995. BioTechn. 13:498-503.

Ward P., Zhou X., Conneely O. M. 1996. J. Biol. Chem. 271:127.90-12794.

Watanabe Y., Barbashov S. F., Komatsu S., Hemmings A. M., Miyagi M., Tsunasawa S., Hirano H. 1994. Eur. J. Biochem. 224:167-172.

Watanabe Y., Hirano H. 1994. Plant Physiol. 105:1019-1020.

Watson J. D., Gilman M., Witkowski J., Zoller M. 1992. Recombinant DNA. W.H. Freeman and Co. New York, p. 213.

Wobus U., Borisjuk L., Panitz R., Manteuffel R., Baumlein H., Wohlfahrt T., Heim U., Weber H., Misera S., Weschke W. 1995. J. Plant Physiol. 145:592-599.

---

The invention claimed is:

1. A plant expression cassette, wherein said expression cassette expresses non-degraded human lactoferrin in seed, said cassette comprising a gene encoding human lactoferrin comprising the sequence SEQ ID NO: 23, said gene being operatively linked to the sequence SEQ ID NO: 21 and a leader sequence encoding a signal peptide of the sequence SEQ ID NO: 26.

2. The plant expression cassette according to claim 1, wherein said leader sequence has the sequence SEQ ID NO: 13.

3. The plant expression cassette according to claim 1, wherein said gene encoding human lactoferrin has the sequence SEQ ID NO: 1.

4. A recombinant DNA vector comprising the plant expression cassette of claim 1.

5. The recombinant DNA vector according to claim 4, wherein said leader sequence has the sequence SEQ ID NO: 13.

6. The recombinant DNA vector according to claim 4, wherein said gene coding for human lactoferrin has the sequence SEQ ID NO: 1.

7. A method for using the vector according to claim 4 for the transformation of vegetal cells comprising:
    transferring said vector in competent *agrobacterium* cells; and
    transforming said vegetal cells with the *agrobacterium* cells obtained from said transferring.

8. A vegetal cell including the vector of claim 4.

9. A cellular aggregation obtained from cells according to claim 8.

10. The cellular aggregation according to claim 9 wherein said aggregation is a callus, and wherein said callus is capable of regenerating a transgenic plant.

11. A transgenic plant, comprising the expression cassette of claim 1, said plant expressing in-seed the non-degraded protein human lactoferrin.

12. The transgenic plant according to claim 11, said plant being selected from the group consisting of solanaceae, cereals and leguminosae.

13. The transgenic plant according to claim 12, said plant being selected from the group consisting of soya, tobacco and rice.

14. A method for using the vector according to claim 4 for transformation of vegetal cells comprising:
    subjecting said cells to bombing with a biolistic system; and
    biolistically transforming said cells with said vector.

15. A method for production of human lactoferrin extracts comprising:
    collecting seeds of the transgenic plant according to claim 11; and
    grinding said seeds in contact with an extraction buffer to produce said human lactoferrin extract.

16. A method of using the transgenic plant according to claim 11 for production of non-degraded human lactoferrin comprising:
    collecting seeds of said transgenic plant;
    grinding said seeds in contact with an extraction buffer; and
    purifying said non-degraded human lactoferrin therefrom.

17. A method for production of human lactoferrin-containing flour comprising:
    collecting seeds of the transgenic plant according to claim 11; and
    grinding said seeds into human lactoferrin-containing flour.

18. A method for production of vegetal milk containing human lactoferrin comprising:
    collecting seeds of the transgenic plant according to claim 11; and
    grinding said seeds into flour and suspending same to produce said vegetal milk.

19. A method for using the vector according to claim 5 for the transformation of vegetal cells comprising:
    transferring said vector in competent *agrobacterium* cells; and
    transforming said vegetal cells with the *agrobacterium* cells obtained from said transferring.

20. A vegetal cell including the vector of claim 5.

21. A cellular aggregation obtained from cells according to claim 20.

22. The cellular aggregation according to claim 21 wherein said aggregation is a callus, and wherein said callus is capable of regenerating a transgenic plant.

23. A transgenic plant, comprising the expression cassette of claim 2, said plant expressing in-seed the non-degraded protein human lactoferrin.

24. The transgenic plant according to claim 23, said plant being selected from the group consisting of solanaceae, cereals and leguminosae.

25. The transgenic plant according to claim 24, said plant being selected from the group consisting of soya, tobacco and rice.

26. A method for using the vector according to claim 5 for transformation of vegetal cells comprising:
- subjecting said cells to bombing with a biolistic system; and
- biolistically transforming said cells with said vector.

27. A method for production of human lactoferrin extracts comprising:
- collecting seeds of the transgenic plant according to claim 23; and
- grinding said seeds in contact with an extraction buffer to produce said human lactoferrin extract.

28. A method of using the transgenic plant according to claim 23 for production of non-degraded human lactoferrin comprising:
- collecting seeds of said transgenic plant;
- grinding said seeds in contact with an extraction buffer; and
- purifying said non-degraded human lactoferrin therefrom.

29. A method for production of human lactoferrin-containing flour comprising:
- collecting the seeds of the transgenic plant according to claim 23; and
- grinding said seeds into human lactoferrin-containing flour.

30. A method for production of vegetal milk containing human lactoferrin comprising:
- collecting seeds of the transgenic plant according to claim 23; and
- grinding said seeds and suspending same to produce said vegetal milk.

31. A method for using the vector according to claim 6 for the transformation of vegetal cells comprising:
- transferring said vector in competent *agrobacterium* cells; and
- transforming said vegetal cells with the *agrobacterium* cells obtained from said transferring.

32. A vegetal cell including the vector of claim 6.

33. A cellular aggregation obtained from cells according to claim 32.

34. The cellular aggregation according to claim 33 wherein said aggregation is a callus, and wherein said callus is capable of regenerating a transgenic plant.

35. A transgenic plant, comprising the expression cassette of claim 3, said plant expressing in-seed the non-degraded protein human lactoferrin.

36. The transgenic plant according to claim 35, said plant being selected from the group consisting of solanaceae, cereals and leguminosae.

37. The transgenic plant according to claim 36, said plant being selected from the group consisting of soya, tobacco and rice.

38. A method for using the vector according to claim 6 for transformation of vegetal cells comprising:
- subjecting said cells to bombing with a biolistic system; and
- biolistically transforming said cells with said vector.

39. A method for production of human lactoferrin extracts comprising:
- collecting seeds of the transgenic plant according to claim 35; and
- grinding said seeds in contact with an extraction buffer to produce said human lactoferrin extract.

40. A method of using the transgenic plant according to claim 35 for production of non-degraded human lactoferrin comprising:
- collecting seeds of said transgenic plant;
- grinding said seeds in contact with an extraction buffer; and
- purifying said non-degraded human lactoferrin therefrom.

41. A method for production of human lactoferrin-containing flour comprising:
- collecting the seeds of the transgenic plant according to claim 35; and
- grinding said seeds into human lactoferrin-containing flour.

42. A method for production of vegetal milk containing human lactoferrin comprising:
- collecting seeds of the transgenic plant according to claim 35; and
- grinding said seeds and suspending same to produce said vegetal milk.

* * * * *

SEQUENCE LISTING

<160> NUMBER OF SEQ ID NOS: 26

<210> SEQ ID NO 1
<211> LENGTH: 2079
<212> TYPE: DNA

<213> ORGANISM: Artificial Sequence
<220> FEATURE:
<223> OTHER INFORMATION: Description of Artificial Sequence: Synthetic human lactoferrin
<220> FEATURE:
<221> NAME/KEY: CDS
<222> LOCATION: (1)..(2076)

<400> SEQUENCE: 1

| | | | | | | | | | | | | | | | | |
|---|---|---|---|---|---|---|---|---|---|---|---|---|---|---|---|---|
| ggc | cgt | agg | aga | agg | agt | gtt | caa | tgg | tgc | gca | gta | tca | caa | cca | gag | 48 |
| Gly | Arg | Arg | Arg | Ser | Val | Gln | Trp | Cys | Ala | Val | Ser | Gln | Pro | Glu | | |
| 1 | | | | 5 | | | | | 10 | | | | | 15 | | |
| gcc | aca | aaa | tgc | ttc | caa | tgg | caa | agg | aat | atg | aga | aaa | gtt | cgt | gga | 96 |
| Ala | Thr | Lys | Cys | Phe | Gln | Trp | Gln | Arg | Asn | Met | Arg | Lys | Val | Arg | Gly | |
| | | 20 | | | | | 25 | | | | | 30 | | | | |
| cct | cct | gta | tct | tgc | ata | aag | aga | gat | tca | ccc | atc | cag | tgt | atc | cag | 144 |
| Pro | Pro | Val | Ser | Cys | Ile | Lys | Arg | Asp | Ser | Pro | Ile | Gln | Cys | Ile | Gln | |
| | | | 35 | | | | | 40 | | | | | 45 | | | |
| gca | att | gcg | gaa | aac | aga | gct | gat | gct | gtg | act | ctt | gat | ggt | ggt | ttc | 192 |
| Ala | Ile | Ala | Glu | Asn | Arg | Ala | Asp | Ala | Val | Thr | Leu | Asp | Gly | Gly | Phe | |
| 50 | | | | | 55 | | | | | 60 | | | | | | |
| ata | tac | gag | gca | gga | ctt | gcc | cca | tac | aaa | ctg | cga | cct | gta | gcg | gcg | 240 |
| Ile | Tyr | Glu | Ala | Gly | Leu | Ala | Pro | Tyr | Lys | Leu | Arg | Pro | Val | Ala | Ala | |
| 65 | | | | | 70 | | | | | 75 | | | | | 80 | |
| gaa | gtc | tac | ggg | acc | gaa | aga | caa | cca | cga | act | cac | tat | tat | gct | gtg | 288 |
| Glu | Val | Tyr | Gly | Thr | Glu | Arg | Gln | Pro | Arg | Thr | His | Tyr | Tyr | Ala | Val | |
| | | | | 85 | | | | | 90 | | | | | 95 | | |
| gct | gtt | gtg | aag | aag | ggc | gga | tct | ttt | cag | ctg | aac | gaa | ctt | caa | ggt | 336 |
| Ala | Val | Val | Lys | Lys | Gly | Gly | Ser | Phe | Gln | Leu | Asn | Glu | Leu | Gln | Gly | |
| | | | 100 | | | | | 105 | | | | | 110 | | | |
| ctg | aag | tca | tgc | cac | aca | gga | ctt | cgc | agg | acc | gct | gga | tgg | aat | gtc | 384 |
| Leu | Lys | Ser | Cys | His | Thr | Gly | Leu | Arg | Arg | Thr | Ala | Gly | Trp | Asn | Val | |
| | | 115 | | | | | 120 | | | | | 125 | | | | |
| cct | ata | ggg | aca | ctt | cgt | cca | ttc | ttg | aat | tgg | acg | ggt | cca | cct | gag | 432 |
| Pro | Ile | Gly | Thr | Leu | Arg | Pro | Phe | Leu | Asn | Trp | Thr | Gly | Pro | Pro | Glu | |
| | 130 | | | | | 135 | | | | | 140 | | | | | |
| ccc | att | gag | gca | gct | gtg | gca | aga | ttc | ttc | tca | gcc | tct | tgt | gtt | cca | 480 |
| Pro | Ile | Glu | Ala | Ala | Val | Ala | Arg | Phe | Phe | Ser | Ala | Ser | Cys | Val | Pro | |
| 145 | | | | | 150 | | | | | 155 | | | | | 160 | |
| ggt | gca | gat | aaa | gga | caa | ttc | ccc | aac | ctt | tgt | cgc | ctg | tgt | gcg | ggg | 528 |
| Gly | Ala | Asp | Lys | Gly | Gln | Phe | Pro | Asn | Leu | Cys | Arg | Leu | Cys | Ala | Gly | |
| | | | 165 | | | | | 170 | | | | | 175 | | | |
| aca | ggg | gaa | aac | aaa | tgt | gca | ttc | tca | tcc | cag | gaa | ccg | tac | ttc | agc | 576 |
| Thr | Gly | Glu | Asn | Lys | Cys | Ala | Phe | Ser | Ser | Gln | Glu | Pro | Tyr | Phe | Ser | |
| | | 180 | | | | | 185 | | | | | 190 | | | | |
| tac | tct | ggt | gcc | ttt | aag | tgt | ctt | aga | gac | ggt | gct | gga | gat | gtt | gct | 624 |
| Tyr | Ser | Gly | Ala | Phe | Lys | Cys | Leu | Arg | Asp | Gly | Ala | Gly | Asp | Val | Ala | |
| | 195 | | | | | 200 | | | | | 205 | | | | | |
| ttt | att | aga | gag | agc | aca | gtg | ttt | gag | gat | ctt | tca | gac | gag | gct | gaa | 672 |
| Phe | Ile | Arg | Glu | Ser | Thr | Val | Phe | Glu | Asp | Leu | Ser | Asp | Glu | Ala | Glu | |
| 210 | | | | | 215 | | | | | 220 | | | | | | |
| agg | gac | gag | tat | gag | tta | ctc | tgc | cca | gac | aac | act | cgt | aag | cca | gtt | 720 |
| Arg | Asp | Glu | Tyr | Glu | Leu | Leu | Cys | Pro | Asp | Asn | Thr | Arg | Lys | Pro | Val | |
| 225 | | | | | 230 | | | | | 235 | | | | | 240 | |
| gac | aag | ttc | aaa | gat | tgc | cat | ctt | gca | cgg | gtc | cct | tct | cat | gcc | gtt | 768 |
| Asp | Lys | Phe | Lys | Asp | Cys | His | Leu | Ala | Arg | Val | Pro | Ser | His | Ala | Val | |
| | | | | 245 | | | | | 250 | | | | | 255 | | |
| gtg | gca | cga | agt | gtt | aat | gga | aag | gag | gat | gcc | atc | tgg | aat | ctt | ctc | 816 |
| Val | Ala | Arg | Ser | Val | Asn | Gly | Lys | Glu | Asp | Ala | Ile | Trp | Asn | Leu | Leu | |
| | | | 260 | | | | | 265 | | | | | 270 | | | |
| cgc | caa | gca | cag | gaa | aag | ttt | gga | aag | gac | aag | tca | ccg | aaa | ttc | cag | 864 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Arg | Gln | Ala | Gln | Glu | Lys | Phe | Gly | Lys | Asp | Lys | Ser | Pro | Lys | Phe | Gln |      |
|     |     | 275 |     |     |     |     | 280 |     |     |     |     | 285 |     |     |     |      |

```
ctc ttt ggt tcc cct agt ggg cag aaa gat ctt ctg ttc aag gac tct      912
Leu Phe Gly Ser Pro Ser Gly Gln Lys Asp Leu Leu Phe Lys Asp Ser
    290             295                 300 gcc att ggg ttt tcg aga gtg cca cct agg ata gat tct ggg ttg tac      960
Ala Ile Gly Phe Ser Arg Val Pro Pro Arg Ile Asp Ser Gly Leu Tyr
305             310                 315                 320 ctt ggc tcc gga tac ttt act gca att cag aac ttg agg aaa agt gag      1008
Leu Gly Ser Gly Tyr Phe Thr Ala Ile Gln Asn Leu Arg Lys Ser Glu
                325                 330                 335 gag gaa gtt gct gcc cgg cgt gcg cgg gtc gtt tgg tgt gcg gtg gga      1056
Glu Glu Val Ala Ala Arg Arg Ala Arg Val Val Trp Cys Ala Val Gly
            340                 345                 350 gag caa gag ttg cgc aag tgt aac cag tgg agt ggt ttg agc gaa gga      1104
Glu Gln Glu Leu Arg Lys Cys Asn Gln Trp Ser Gly Leu Ser Glu Gly
        355                 360                 365 tct gtg acc tgc tca tcg gcc tcc act aca gaa gat tgc atc gcc ctg      1152
Ser Val Thr Cys Ser Ser Ala Ser Thr Thr Glu Asp Cys Ile Ala Leu
    370                 375                 380 gtg ttg aaa gga gaa gct gat gcc atg agt ttg gat gga gga tat gtt      1200
Val Leu Lys Gly Glu Ala Asp Ala Met Ser Leu Asp Gly Gly Tyr Val
385                 390                 395                 400 tac act gca ggt aaa tgt ggt ttg gtc cct gtc ctt gca gag aac tac      1248
Tyr Thr Ala Gly Lys Cys Gly Leu Val Pro Val Leu Ala Glu Asn Tyr
                405                 410                 415 aaa tca caa caa agc agt gac cct gat cct aac tgt gtg gat aga cct      1296
Lys Ser Gln Gln Ser Ser Asp Pro Asp Pro Asn Cys Val Asp Arg Pro
            420                 425                 430 gtg gaa gga tat ctt gct gtg gcg gtg gtt agg aga tca gac act agc      1344
Val Glu Gly Tyr Leu Ala Val Ala Val Val Arg Arg Ser Asp Thr Ser
        435                 440                 445 ctt acc tgg aac tct gtg aaa ggc aag aag tcc tgc cac acc gcc gtg      1392
Leu Thr Trp Asn Ser Val Lys Gly Lys Lys Ser Cys His Thr Ala Val
    450                 455                 460 gac agg act gca ggt tgg aat atc ccc atg gga ttg ctc ttc aac cag      1440
Asp Arg Thr Ala Gly Trp Asn Ile Pro Met Gly Leu Leu Phe Asn Gln
465                 470                 475                 480 acg ggc tcc tgc aaa ttt gat gaa tat ttc agt caa agc tgt gcc cct      1488
Thr Gly Ser Cys Lys Phe Asp Glu Tyr Phe Ser Gln Ser Cys Ala Pro
                485                 490                 495 ggt tct gac cca aga tct aat ctc tgt gct ttg tgt att gga gat gag      1536
Gly Ser Asp Pro Arg Ser Asn Leu Cys Ala Leu Cys Ile Gly Asp Glu
            500                 505                 510 caa ggt gag aat aag tgc gtt ccc aac agc aac gag aga tac tac ggt      1584
Gln Gly Glu Asn Lys Cys Val Pro Asn Ser Asn Glu Arg Tyr Tyr Gly
        515                 520                 525 tac act ggg gct ttc cgt tgc ttg gct gag aat gct gga gac gtt gca      1632
Tyr Thr Gly Ala Phe Arg Cys Leu Ala Glu Asn Ala Gly Asp Val Ala
    530                 535                 540 ttt gtg aaa gat gtc act gtc ttg cag aac act gat gga aat aac aat      1680
Phe Val Lys Asp Val Thr Val Leu Gln Asn Thr Asp Gly Asn Asn Asn
545                 550                 555                 560 gag gca tgg gct aag gat ttg aag ctt gca gac ttt gcg ttg ctg tgc      1728
Glu Ala Trp Ala Lys Asp Leu Lys Leu Ala Asp Phe Ala Leu Leu Cys
                565                 570                 575 ctc gat ggc aaa cgt aag cct gtg act gaa gct aga agc tgc cat ctt      1776
Leu Asp Gly Lys Arg Lys Pro Val Thr Glu Ala Arg Ser Cys His Leu
            580                 585                 590
```

-continued

```
gcc atg gcc ccg aat cat gct gtg gtg tct cgt atg gat aag gtg gaa      1824
Ala Met Ala Pro Asn His Ala Val Val Ser Arg Met Asp Lys Val Glu
        595                 600                 605 cgc ttg aaa cag gtg ttg ctc cac caa cag gct aaa ttt ggt aga aat      1872
Arg Leu Lys Gln Val Leu Leu His Gln Gln Ala Lys Phe Gly Arg Asn
    610                 615                 620 gga tct gac tgc ccg gac aag ttt tgc tta ttc cag tct gaa acc aaa      1920
Gly Ser Asp Cys Pro Asp Lys Phe Cys Leu Phe Gln Ser Glu Thr Lys
625                 630                 635                 640 aac ctt ttg ttc aat gac aac act gag tgt ctt gcc aga ctc cat ggc      1968
Asn Leu Leu Phe Asn Asp Asn Thr Glu Cys Leu Ala Arg Leu His Gly
                645                 650                 655 aaa aca aca tat gaa aaa tat ttg gga cca cag tat gtc gca ggc att      2016
Lys Thr Thr Tyr Glu Lys Tyr Leu Gly Pro Gln Tyr Val Ala Gly Ile
            660                 665                 670 act aat ctg aaa aag tgc tca acc tcc cca ctc cta gaa gcc tgt gaa      2064
Thr Asn Leu Lys Lys Cys Ser Thr Ser Pro Leu Leu Glu Ala Cys Glu
        675                 680                 685 ttc cta agg aag taa                                                   2079
Phe Leu Arg Lys
    690
```

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 2
ggatccatgg gccgtaggag aaggagtgtt                                     30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gagctccttc ggttttactt cctgaggaat tc                                  32

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
tctagataaa ataatctata cattaaaaaa tttgatttta aa                       42

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
ggatccgact gagtcggata agaagaaaag aaaaga                              36

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
tctagagttt tcaaatttga attttaatgt gtgttg                                36

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ggatcccacc ttaaggaggt tgcaacgagc gtggca                                36

<210> SEQ ID NO 8
<211> LENGTH: 250
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ggccgtagga gaaggagtgt tcaatggtgc gcagtatcac aaccagaggc cacaaaatgc      60
ttccaatggc aaaggaatat gagaaaagtt cgtggacctc ctgtatcttg cataaagaga     120
gattcaccca tccagtgtat ccaggcaatt gcggaaaaca gagctgatgc tgtgactctt     180
gatggtggtt tcatatacga ggcaggactt gccccataca aactgcgacc tgtagcggcg     240
gaagtctacg                                                            250

<210> SEQ ID NO 9
<211> LENGTH: 250
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gcacctggaa cacaagaggc tgagaagaat cttgccacag ctgcctcaat gggctcaggt      60
ggacccgtcc aattcaagaa tggacgaagt gtccctatag gacattcca tccagcggtc     120 ctgcgaagtc ctgtgtggca tgacttcaga ccttgaagtt cgttcagctg aaaagatccg     180
cccttcttca caacagccac agcataatag tgagttcgtg gttgtctttc ggtcccgtag     240
acttccgccg                                                            250

<210> SEQ ID NO 10
<211> LENGTH: 250
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10

-continued

```
aactggctta cgagtgttgt ctgggcagag taactcatac tcgtccctttt cagcctcgtc    60 tgaaagatcc tcaaacactg tgctctctct aataaaagca acatctccag caccgtctct   120
aagacactta aaggcaccag agtagctgaa gtacggttcc tgggatgaga atgcacattt   180
gttttcccct gtccccgcac acaggcgaca aaggttgggg aattgtcctt tatctgcacc   240
tggaacacaa                                                          250
```

<210> SEQ ID NO 11
<211> LENGTH: 255
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11

```
gtacaaccca gaatctatcc taggtggcac tctcgaaaac ccaatggcag agtccttgaa    60
cagaagatct ttctgcccac taggggaacc aaagagctgg aatttcggtg acttgtcctt   120
tccaaacttt tcctgtgctt ggcggagaag attccagatg gcatcctcct ttccattaac   180
acttcgtgcc acaacggcat gagaagggac ccgtgcaaga tggcaatctt tgaacttgtc   240
aactggctta cgagt                                                    255
```

<210> SEQ ID NO 12
<211> LENGTH: 251
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12

```
tatcctccat ccaaactcat ggcatcagct tctcctttca acaccagggc gatgcaatct    60
tctgtagtgg aggccgatga gcaggtcaca gatccttcgc tcaaaccact ccactggtta   120
cacttgcgca actcttgctc tcccaccgca caccaaacga cccgcgcacg ccgggcagca   180
acttcctcct cactttttcct caagttctga attgcagtaa agtatccgga gccaaggtac   240
aacccagaat c                                                        251
```

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13

```
atggcttcta tcctccacta ctttttagcc ctctctcttt cttgctcttt tcttttcttc    60
ttatccgact cagtc                                                    75
```

<210> SEQ ID NO 14
<211> LENGTH: 189
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14

```
atgatgagag cgcggttccc attactgttg ctgggagttg ttttcctagc atcagtttct    60
gtctcatttg gcattgcgta ttgggaaaag cagaacccca gtcacaacaa gtgcctccga   120
agttgcaata gcgagaaaga ctcctacagg aaccaagcat gccacgctcg ttgcaacctc   180
cttaaggtg                                                          189
```

<210> SEQ ID NO 15
<211> LENGTH: 250
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15

```
gagcaatccc atgggatat tccaacctgc agtcctgtcc acggcggtgt ggcaggactt     60
cttgcctttc acagagttcc aggtaaggct agtgtctgat ctcctaacca ccgccacagc   120
aagatatcct tccacaggtc tatccacaca gttaggatca gggtcactgc tttgttgtga   180
tttgtagttc tctgcaagac aggcaccaaa ccacatttac ctgcagtgta aacatatcct   240
ccatccaaac                                                         250
```

<210> SEQ ID NO 16
<211> LENGTH: 254
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16

```
ccatcagtgt tctgcaagac agtgacatct ttcacaaatg caacgtctcc agcattctca    60
gccaagcaac ggaaagcccc agtgtaaccg tagtatctct cgttgctgtt gggaacgcac   120
ttattctcac cttgctcatc tccaatacac aaagcacaga gattagatct tgggtcagaa   180
ccaggggcac agctttgact gaaatattca tcaaatttgc aggagcccgt ctggttgaag   240
agcaagccca tggg                                                    254
```

<210> SEQ ID NO 17
<211> LENGTH: 229
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17

```
gcagtcagat ccatttctac caaatttagc ctgttggtgg agcaacacct gtttcaagcg    60
ttccacctta tccatacgag acaccacagc atgattcggg gccatggcaa gatggcagct   120
tctagcttca gtcacaggct tacgtttgcc atcgaggcac agcaacgcaa agtctgcaag   180
cttcaaatcc ttagcccatg cctcattgtt atttccatca gtgttctgc                229
```

<210> SEQ ID NO 18
<211> LENGTH: 210
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18

```
ttacttcctt aggaattcac aggcttctag gagtgggag gttgagcact ttttcagatt      60
agtaatgcct gcgacatact gtggtcccaa atatttttca tatgttgttt tgccatggag    120
tctggcaaga cactcagtgt tgtcattgaa caaaaggttt ttggtttcag actggaataa    180
gcaaaacttg tccgggcagt cagatccatt                                     210
```

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19

```
ggatccatgg gccgtaggag aaggagtgtt                                      30
```

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20

```
gagctcttac ttccttagga attcacag                                        28
```

<210> SEQ ID NO 21
<211> LENGTH: 1367
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21

```
taaaataatc tatacattaa aaaatttgat tttaaaattt tagaaattca tgattttatt     60
tttttttacc agaaatccgt taatattgtt aaaatattac caactaattt ataaatttta   120
ttttaaggca attaagcatg tttgataaaa tatatatatt gttataaata cttttcaaaa   180
gtataaagtt gatgatggcg tggtggtaga ttattttagt tctaggttcg aatgcaagtt   240
ggtttagaca tttagcccta ttcttttttc taaccaaaat aaatgtaaat ggaaaacctt   300
taggaaaaaa aagaaatcaa aattgaaaac atcatccggt ggagtcgaga agcccacacc   360
cacgtgaccc aacaatatta aaataagagt ttgctctaca gtaaatgcga tactttttta   420
ttcaatactt tttccacttc taaaatcttg gagatttgca ccgttaacta attaagtgtt   480
atatccaacg gtcctaaaaa aacttgtgta ccgtgcctca catttcaact ttgcgcaccc   540
tgaaagccgt tatgtttagg ttagtgtttg caacagttga agcgcatcac tcaggaggct   600
acttggtctt gcttttgcgt cttttgttca attttcacg tgattttgtt ggtgaacacg    660
cgtacttgaa acttattata aattacataa ttttataagt ttcacttctt atataatact   720
catataatat atagggttta gaatgccaat ttttaaaaaa agaataaaaa aataaataga   780
ataaaatcga aaaatgaaa tgtaaaaaat ttgaggggga caaataaaat atgaaagtct   840
attatttaaa ttttccatta gaattctatt ttccttagtt aatatgagct agccagttgg   900
gagatacacg aaaatgtcat gaacagttga catgtaggga aattaatgta gtagagggat   960
agcaagacaa aaatccaagc caagctagct gctcacgcga actcgatcca cacgtccttt  1020
```

-continued

```
acagagtttc aaacggatga aatctgcatg gcatgcaact aaagcattgt tctcagctgc    1080
caagtacccc tcacactcac caacccttttg tttttctccc cattgcatgt taactcaagt    1140
ttatcctttc tttgcttctg gaaatttcac aagcctcaaa cacgtcgacg tccaatcttg    1200
tgaccaacac ggccaaaaga aaagagaatc tcatcccgtt cacacttagc cacttaaagc    1260
tagccaaacg gtgatctttc tctatatatt gtagctctct aacacaacca acactaccat    1320
tattcaatat tcaaaccttg ctctatacta cacacactag aagaata               1367
```

<210> SEQ ID NO 22
<211> LENGTH: 962
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22

```
gttttcaaat ttgaatttta atgtgtgttg taagtataaa tttaaaataa aaataaaaac    60
aattattata tcaaaatggc aaaaacattt aatacgtatt attttattaaa aaatatgta    120 ataatatatt tatattttaa tatctattct tatgtatttt ttaaaaatct attatatatt    180
gatcaactaa aatattttta tatctacact tattttgcat ttttatcaat tttcttgcgt    240
tttttggcat atttaataat gactattctt taataatcaa tcattattct tacatggtac    300
atattgttgg aaccatatga agtgttcatt gcatttgact atgtggatag tgttttgatc    360
catgcccttc atttgccgct attaattaat ttggtaacag attcgttcta atcagttact    420
taatccttcc tcatcataat taatctggta gttcgaatgc cataaatttg attagttttt    480
tggaccataa gaaaaagcca aggaacaaaa gaagacaaaa cacaatgaga gtatcctttg    540
catagcaatg tctaagttca taaaattcaa acaaaaacgc aatcacacac agtggacatc    600
acttatccac tagctgatca ggatcgccgc gtcaagaaaa aaaaactgga ccccaaaagc    660
catgcacaac aacacgtact cacaaaggcg tcaatcgagc agcccaaaac attcaccaac    720
tcaacccatc atgagcccac acatttgttg tttctaaccc aacctcaaac tcgtattctc    780
ttccgccacc tcattttgt ttatttcaac acccgtcaaa ctgcatccca ccccgtggcc    840
aaatgttcat gcatgttaac aagacctatg actataaata tctgcaatct cggcccaagt    900
tttcatcatc aagaaccagt tcaatatcct agtacgccgt attaaagaat ttaagatata    960
ct                                                                    962
```

<210> SEQ ID NO 23
<211> LENGTH: 692
<212> TYPE: PRT
<213> ORGANISM: Artificial Sequence
<220> FEATURE:
<223> OTHER INFORMATION: Description of Artificial Sequence: Synthetic
      human lactoferrin

<400> SEQUENCE: 23

Gly Arg Arg Arg Arg Ser Val Gln Trp Cys Ala Val Ser Gln Pro Glu
 1               5                  10                  15

Ala Thr Lys Cys Phe Gln Trp Gln Arg Asn Met Arg Lys Val Arg Gly
            20                  25                  30

Pro Pro Val Ser Cys Ile Lys Arg Asp Ser Pro Ile Gln Cys Ile Gln
        35                  40                  45

Ala Ile Ala Glu Asn Arg Ala Asp Ala Val Thr Leu Asp Gly Gly Phe

-continued

```
              50                  55                  60
Ile Tyr Glu Ala Gly Leu Ala Pro Tyr Lys Leu Arg Pro Val Ala Ala
 65                  70                  75                  80

Glu Val Tyr Gly Thr Glu Arg Gln Pro Arg Thr His Tyr Tyr Ala Val
                 85                  90                  95

Ala Val Val Lys Lys Gly Gly Ser Phe Gln Leu Asn Glu Leu Gln Gly
            100                 105                 110

Leu Lys Ser Cys His Thr Gly Leu Arg Arg Thr Ala Gly Trp Asn Val
            115                 120                 125

Pro Ile Gly Thr Leu Arg Pro Phe Leu Asn Trp Thr Gly Pro Pro Glu
130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
            195                 200                 205

Phe Ile Arg Glu Ser Thr Val Phe Glu Asp Leu Ser Asp Glu Ala Glu
210                 215                 220

Arg Asp Glu Tyr Glu Leu Leu Cys Pro Asp Asn Thr Arg Lys Pro Val
225                 230                 235                 240

Asp Lys Phe Lys Asp Cys His Leu Ala Arg Val Pro Ser His Ala Val
                245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
            275                 280                 285

Leu Phe Gly Ser Pro Ser Gly Gln Lys Asp Leu Leu Phe Lys Asp Ser
290                 295                 300

Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
                325                 330                 335

Glu Glu Val Ala Ala Arg Arg Ala Arg Val Val Trp Cys Ala Val Gly
            340                 345                 350

Glu Gln Glu Leu Arg Lys Cys Asn Gln Trp Ser Gly Leu Ser Glu Gly
            355                 360                 365

Ser Val Thr Cys Ser Ser Ala Ser Thr Thr Glu Asp Cys Ile Ala Leu
370                 375                 380

Val Leu Lys Gly Glu Ala Asp Ala Met Ser Leu Asp Gly Gly Tyr Val
385                 390                 395                 400

Tyr Thr Ala Gly Lys Cys Gly Leu Val Pro Val Leu Ala Glu Asn Tyr
                405                 410                 415

Lys Ser Gln Gln Ser Ser Asp Pro Asp Pro Asn Cys Val Asp Arg Pro
            420                 425                 430

Val Glu Gly Tyr Leu Ala Val Ala Val Val Arg Arg Ser Asp Thr Ser
            435                 440                 445

Leu Thr Trp Asn Ser Val Lys Gly Lys Lys Ser Cys His Thr Ala Val
450                 455                 460

Asp Arg Thr Ala Gly Trp Asn Ile Pro Met Gly Leu Leu Phe Asn Gln
465                 470                 475                 480
```

```
Thr Gly Ser Cys Lys Phe Asp Glu Tyr Phe Ser Gln Ser Cys Ala Pro
            485                 490                 495
Gly Ser Asp Pro Arg Ser Asn Leu Cys Ala Leu Cys Ile Gly Asp Glu
        500                 505                 510
Gln Gly Glu Asn Lys Cys Val Pro Asn Ser Asn Glu Arg Tyr Tyr Gly
    515                 520                 525
Tyr Thr Gly Ala Phe Arg Cys Leu Ala Glu Asn Ala Gly Asp Val Ala
530                 535                 540
Phe Val Lys Asp Val Thr Val Leu Gln Asn Thr Asp Gly Asn Asn Asn
545                 550                 555                 560
Glu Ala Trp Ala Lys Asp Leu Lys Leu Ala Asp Phe Ala Leu Leu Cys
            565                 570                 575
Leu Asp Gly Lys Arg Lys Pro Val Thr Glu Ala Arg Ser Cys His Leu
        580                 585                 590
Ala Met Ala Pro Asn His Ala Val Val Ser Arg Met Asp Lys Val Glu
    595                 600                 605
Arg Leu Lys Gln Val Leu Leu His Gln Gln Ala Lys Phe Gly Arg Asn
610                 615                 620
Gly Ser Asp Cys Pro Asp Lys Phe Cys Leu Phe Gln Ser Glu Thr Lys
625                 630                 635                 640
Asn Leu Leu Phe Asn Asp Asn Thr Glu Cys Leu Ala Arg Leu His Gly
            645                 650                 655
Lys Thr Thr Tyr Glu Lys Tyr Leu Gly Pro Gln Tyr Val Ala Gly Ile
        660                 665                 670
Thr Asn Leu Lys Lys Cys Ser Thr Ser Pro Leu Leu Glu Ala Cys Glu
    675                 680                 685
Phe Leu Arg Lys
    690

<210> SEQ ID NO 24
<211> LENGTH: 1157
<212> TYPE: DNA
<213> ORGANISM: Artificial Sequence
<220> FEATURE:
<223> OTHER INFORMATION: Description of Artificial Sequence: Synthetic
      DNA gmbpsp

<400> SEQUENCE: 24
tctagagttt tcaaatttga attttaatgt gtgttgtaag tataaattta aaataaaaat      60
aaaaacaatt attatatcaa aatggcaaaa catttaatac gtattattta ttaaaaaaat    120
atgtaataat atatttatat tttaatatct attcttatgt atttttttaaa aatctattat   180
atattgatca actaaaatat ttttatatct acacttattt tgcattttta tcaatttct    240
tgcgttttt ggcatattta atgactat tctttaataa tcaatcatta ttccttacatg    300
gtacatattg ttggaaccat atgaagtgtt cattgcattt gactatgtgg atagtgtttt   360
gatccatgcc cttcatttgc cgctattaat taatttggta acagattcgt tctaatcagt   420
tacttaatcc ttcctcatca taattaatct ggtagttcga atgccataat attgattagt   480
ttttggacc ataagaaaaa gccaaggaac aaagaagac aaaacacatg agagtatcct     540
ttgcatagca atgtctaagt tcataaaatt caaacaaaaa cgcaatcaca cacagtggac    600
atcacttatc cactagctga tcaggatcgc cgcgtcaaga aaaaaaaact ggaccccaaa    660
agccatgcac aacaacacgt actcacaaag gcgtcaatcg agcgcccaaa acattcacca    720
actcaaccca tcatgagccc acacatttgt tgtttctaac ccaacctcaa actcgtattc    780
```

-continued

```
tcttccgcca ctcattttg tttatttcaa cacccgtcaa actgcatccc accccgtggc      840
caaatgttca tgcatgttaa caagacctat gactataaat atctgcaatc tcggcccaag     900
ttttcatcat caagaaccag ttcaatatcc tagtacgccg tattaaagaa tttaagatat     960
actatgatga gagcgcggtt cccattactg ttgctgggag ttgttttcct agcatcagtt    1020
tctgtctcat ttggcattgc gtattgggaa aagcaaaccc cagtcacaac aagtgcctcc    1080
gaagttgcaa tagcgagaaa gactcctaca ggaaccaagc atgccacgct cgttgcaacc    1140
tccttaaggt gggatcc                                                   1157
```

<210> SEQ ID NO 25
<211> LENGTH: 1164
<212> TYPE: DNA
<213> ORGANISM: Artificial Sequence
<220> FEATURE:
<223> OTHER INFORMATION: Description of Artificial Sequence: Synthetic
      DNA PCONGT7Sp6
<220> FEATURE:
<221> NAME/KEY: modified_base
<222> LOCATION: (534)
<223> OTHER INFORMATION: a, t, c, g, other or unknown
<220> FEATURE:
<221> NAME/KEY: modified_base
<222> LOCATION: (763)
<223> OTHER INFORMATION: a, t, c, g, other or unknown
<220> FEATURE:
<221> NAME/KEY: modified_base
<222> LOCATION: (787)
<223> OTHER INFORMATION: a, t, c, g, other or unknown
<220> FEATURE:
<221> NAME/KEY: modified_base
<222> LOCATION: (789)
<223> OTHER INFORMATION: a, t, c, g, other or unknown
<220> FEATURE:
<221> NAME/KEY: modified_base
<222> LOCATION: (878)
<223> OTHER INFORMATION: a, t, c, g, other or unknown

<400> SEQUENCE: 25

```
tctagagttt tcaaatttga attttaatgt gtgttgtaag tataaattta aaataaaaat      60
aaaaacaatt attatatcaa aatggcaaaa acatttaata cctattattt aagaaaaaaa     120
tatgtaataa tatatttata tttaatatc tattcttatg tattttttaa aaatctatta     180
tatattgatc aactaaaata ttttatatc tacacttatt ttgcattttt atcaatttc      240 ttgcgtttt tggcatattt aataatgact attctttaat aattaatcat tattcttaca     300
tcgtacatat tgttggaacc atatgaagtg tccattgcat tcgactatgt ggatagtgtt    360
ttgatccagg cctccatttg ccgcttatta attaatttgg taacagtccg tactaatcag    420
ttacttatcc ttcctccatc ataattaatc ttggtagtct cgaatgccac aacactgact    480
agtctcttgg atcataagaa aaagccaaga acaaaggag acaaaacaca atgnagagta    540
tcctttgcat agcaatgtct aagttcataa aattcaaaca aaaacgcaat cacacacagt    600
gggacatcac ttatccacta gctgatcagg atcgccgcgt caagaaaaaa aaaactggga    660
cccaaaagcc atgcacaaca acacgtactc acaaggtgt caatcgagca gcccaaaaca    720
ttcaccaact caacccatca tgagcccaca catttgttgt ttntaaccca acctcaaact    780
cgtattntnt tccgccacct cattttgtt tattccaaca cccgtcaaac tgcatgccac     840
cccgtggcca aatgtccatg catgttaaca agacctanga ctataaatat ctgcaatctc    900
ggcccaggtt ttcatcatca agaaccagtt caatatccta gtacaccgta ttaaagaatt    960
taagatatac tatgatgaga gcgcggttcc cattactgtt gctggagttg ttttcctggc   1020
```

```
-continued atcagtttct gtctcatttg gcattgcgta ttgggaaaag cagaacccca gtcacaacaa      1080
gtgcctccga agttggaaat gcgagaagac tcctacagga accaagcatg ccacgctcgt      1140
tgcaacctcc ttaaggtggg atcc                                              1164

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence: Synthetic
      signal peptide

<400> SEQUENCE: 26

Met Ala Ser Ile Leu His Tyr Phe Leu Ala Leu Ser Leu Ser Cys Ser
 1               5                  10                  15

Phe Leu Phe Phe Leu Ser Asp Ser Val
            20                  25
```